United States Patent
Needle et al.

(10) Patent No.: US 8,372,045 B2
(45) Date of Patent: Feb. 12, 2013

(54) CONTROLLED-VOLUME INFUSION DEVICE

(75) Inventors: Stanley A. Needle, Louisville, CO (US); Andrew N. Lamborne, Denver, CO (US)

(73) Assignee: Curlin Medical Inc., East Aurora, NY (US)

( * ) Notice: Subject to any disclaimer, the term of this patent is extended or adjusted under 35 U.S.C. 154(b) by 1912 days.

(21) Appl. No.: 11/283,091

(22) Filed: Nov. 18, 2005

(65) Prior Publication Data
US 2006/0122562 A1 Jun. 8, 2006

Related U.S. Application Data

(60) Provisional application No. 60/629,795, filed on Nov. 19, 2004.

(51) Int. Cl.
*A61M 5/00* (2006.01)

(52) U.S. Cl. .......................................................... 604/246

(58) Field of Classification Search .............. 604/80–85, 604/183–187, 246–259, 236, 133–136, 191, 604/207–209, 218–231, 132, 151–155
See application file for complete search history.

(56) References Cited

U.S. PATENT DOCUMENTS

| | | | |
|---|---|---|---|
| 3,468,308 A | 9/1969 | Bierman | |
| 4,588,394 A | 5/1986 | Schulte et al. | |
| 4,608,042 A | 8/1986 | Vanderveen et al. | |
| 4,781,689 A | 11/1988 | Sealfon et al. | |
| 4,857,059 A | 8/1989 | Rey et al. | |
| 4,904,243 A | 2/1990 | Bruera | |
| 5,011,477 A | 4/1991 | Winchell et al. | |
| 5,061,243 A | 10/1991 | Winchell et al. | |
| 5,135,491 A | 8/1992 | Baldwin | |
| 5,188,603 A | 2/1993 | Vaillancourt | |
| 5,211,632 A | 5/1993 | Tsukada | |
| 5,224,934 A | 7/1993 | Payne et al. | |
| 5,304,153 A | 4/1994 | Tsujikawa | |
| 5,505,707 A | 4/1996 | Manzie et al. | |
| 5,697,919 A | 12/1997 | Kinoshita et al. | |
| 5,776,103 A | 7/1998 | Kriesel et al. | |
| 5,779,676 A | 7/1998 | Kriesel et al. | |
| 5,807,312 A | 9/1998 | Dzwonkiewicz | |
| 5,891,102 A | 4/1999 | Hiejima et al. | |
| 5,897,527 A | 4/1999 | Tsukada | |
| 5,906,597 A | 5/1999 | McPhee | |
| 5,925,017 A | 7/1999 | Kriesel et al. | |
| 6,024,724 A | 2/2000 | Lee | |
| 6,045,533 A | 4/2000 | Kriesel et al. | |
| 6,056,727 A * | 5/2000 | O'Neil .......................... | 604/183 |

(Continued)

FOREIGN PATENT DOCUMENTS

| | | |
|---|---|---|
| EP | 0584569 A2 | 3/1994 |
| EP | 0803260 A2 | 10/1997 |

(Continued)

*Primary Examiner* — Nicholas Lucchesi
*Assistant Examiner* — Pritesh Patel
(74) *Attorney, Agent, or Firm* — Hodgson Russ LLP

(57) ABSTRACT

An infusion device capable of administering liquid medication at a continuous flow rate, and upon user demand delivers a controlled volume dosage of liquid medication at a higher dosage flow rate. The dosage reservoir remains empty until the user actuates it by selectively and temporarily removing the pressure source, such as a spring. During actuation, fluid rapidly flows from the medication reservoir to fill the dosage reservoir. After actuation, the pressure source exerts a higher pressure on the dosage reservoir than the medication reservoir pressure, which results in a temporary higher bolus flow rate. Thus, two distinct flow rates are achieved with one flow restrictor element.

26 Claims, 26 Drawing Sheets

U.S. PATENT DOCUMENTS

| | | |
|---|---|---|
| 6,206,850 B1 | 3/2001 | O'Neil |
| 6,213,981 B1 | 4/2001 | Hiejima et al. |
| 6,270,481 B1 | 8/2001 | Mason et al. |
| 6,283,944 B1 | 9/2001 | McMullen et al. |
| 6,312,411 B1 | 11/2001 | Kanai |
| 6,416,495 B1 | 7/2002 | Kriesel et al. |
| 6,471,675 B1 | 10/2002 | Rogers et al. |
| 6,500,156 B1 | 12/2002 | Stansbury |
| 6,530,901 B1 | 3/2003 | Tsukada et al. |
| 6,554,822 B1 | 4/2003 | Holschneider et al. |
| 6,719,728 B2 | 4/2004 | Mason et al. |
| 6,936,035 B2 | 8/2005 | Rake et al. |
| 2002/0123735 A1 | 9/2002 | Rake et al. |
| 2003/0040722 A1 | 2/2003 | Massengale et al. |
| 2003/0050623 A1 | 3/2003 | Lord et al. |
| 2003/0105428 A1 | 6/2003 | Hogan et al. |
| 2004/0059315 A1 | 3/2004 | Erickson et al. |
| 2004/0127860 A1 | 7/2004 | Rake et al. |

FOREIGN PATENT DOCUMENTS

| | | |
|---|---|---|
| EP | 0941741 A2 | 9/1999 |

* cited by examiner

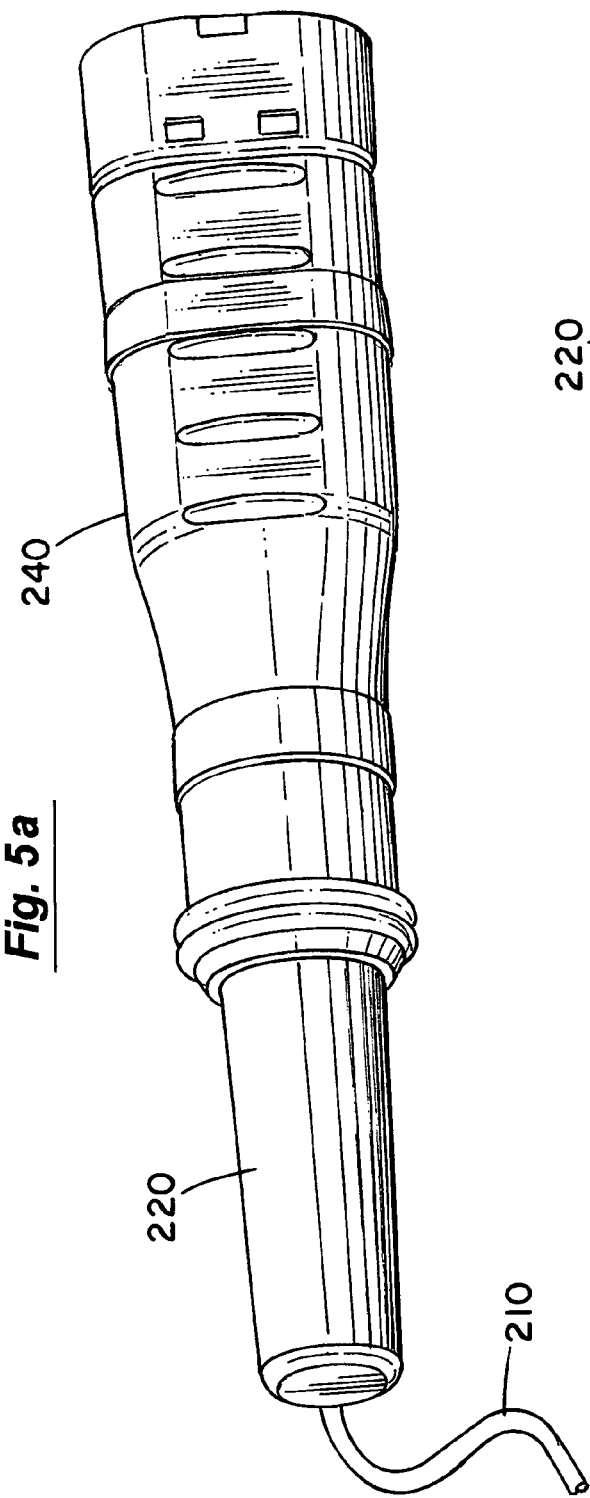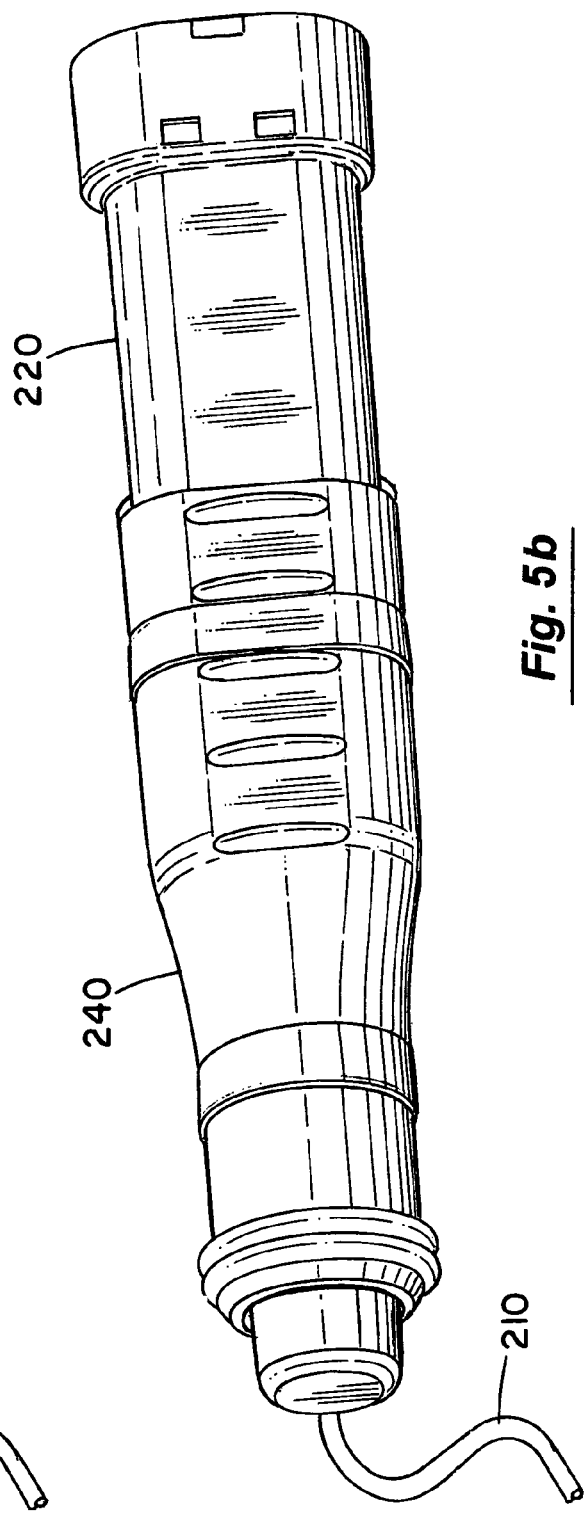

CONTROLLED-VOLUME INFUSION DEVICE

RELATED APPLICATION

The present application is based on and claims priority to the Applicants' U.S. Provisional Patent Application 60/629,795, entitled "Controlled-Volume Infusion Device," filed on Nov. 19, 2004.

BACKGROUND OF THE INVENTION

1. Field of the Invention

This invention relates generally to the field of infusion pumps. More specifically, this invention relates to an improved device and method for administering a series of controlled-volume dosages of fluid, by themselves or in supplement to a continuous infusion of fluid to deliver a liquid medication to a patient.

2. Prior Art

Infusion pumps have been widely used for many years to administer medications and other fluids to patients. Conventional disposable (single-use) infusion pumps administer a substantially continuous flow of fluid. Examples of such infusion pumps include spring-type and vacuum-type syringe pumps, and balloon-type pumps. Conventional electronic, multiple-use infusion pumps may be programmed to provide a variety of flow regimes such as continuous flow, intermittent flow, and variable flow profiles combining the two. Examples of such infusion pumps include peristaltic pumps, screw-driven syringe pumps, and diaphragm pumps.

In certain applications, infusion of a series of discrete dosages, either alone or in conjunction with a continuous flow, has proven to be beneficial. One such example is in treatment of infections and other medical ailments, where standard clinical practice is to administer a series of dosages over a period of time, each dosage in the series being of controlled volume and infused at a controlled rate of flow. These dosages may be administered alone, with no infusion occurring in the time between dosages, or may be administered with a continuous "keep vein open" or "KVO" flow between dosages to maintain patency of the infusion catheter. Depending on the therapy and drug concentration being used, the size of the controlled-volume dosage may vary from a relatively small dosage of a few cc's or less to a relatively large dosage of 25 to 100 cc's or more.

The problem with conventional electronic pumps used in this application is that electronic pumps tend to be relatively expensive, complex to use and maintain, and inconvenient for use in alternate care sites such as the patient's home. The problem with conventional disposable pumps used in this application is that the pumps are designed to dispense a single dose of medication, and cannot be reused for subsequent dosages without risk of contamination. This requires extra effort by the healthcare provider to prepare multiple pumps, and entails additional expense to purchase multiple pumps.

Some disposable pumps are equipped to provide a series of small dosages, but the size of the dosage is limited to 0.5, 1 or 2 cc's. These devices do not provide a large enough dosage volume to be used for many applications.

Another such example is infusion of pain control medications, where a "patient-controlled analgesia" (PCA) pump can be used to provide a patient-controlled bolus dosage of medication, selectively administered by the patient as needed. Existing PCA pumps take the form of "bolus-only" devices, where the bolus dosages are administered alone, or "basal-bolus" devices where the bolus dosages are supplementary to a continuous basal flow. The state of the art and generally accepted clinical practice requires that a PCA pump have a safety feature that limits the infusion rate to a safe dosage, should the patient attempt to continually administer bolus dosages at a rate that would exceed a safe level of medication intake.

Currently available electronic PCA pumps generally provide the necessary performance, including the ability to program the bolus infusion rate such that the bolus dosage is administered over a longer period of time if desired. However, these electronic pumps tend to be relatively expensive, complex to use and maintain, and inconvenient for use in alternate care sites such as the patient's home.

There are a limited number of available options in disposable PCA pumps that meet this requirement, and their typical function is as follows:

- The device provides a medication storage reservoir and a separate bolus dosage reservoir.
- The device provides a flowrate-controlling flow restrictor element that limits the rate at which fluid can flow from the medication storage reservoir into the bolus dosage reservoir; this provides the safety mechanism to limit the maximum infusion rate regardless of how often the user attempts to administer a bolus.
- The device provides a mechanism whereby the user expels the fluid (the bolus dose) in the bolus dosage reservoir; the typical mechanism is a push button or lever than transmits force from the patient's finger or thumb to compress the bolus dosage reservoir, thereby administering the bolus fluid at a rapid infusion rate.
- If the device is a basal-bolus model, it provides a second flowrate-controlling flow restrictor element that limits the speed with which fluid can flow from the medication storage reservoir directly to the patient. This basal flow is typically a parallel flow path that bypasses the bolus dosage reservoir.

One problem with currently available disposable PCA devices is that they are not well suited for large bolus dosage volumes. Typical disposable PCA devices have a 0.5, 1, or 2 cc bolus dosage volume. Larger bolus dosage volumes of 5, 10, or more cc's have been shown to be clinically efficacious, but impractical with currently-available PCA devices.

Manual force from the patient is required to administer the bolus dosage, and larger dosage volumes require greater manual effort; the manual effort that would be required to administer a large bolus dosage can be a burden on patients in a weakened state. Because only the force of the patient's finger or thumb is flushing the bolus dosage out, existing devices require the patient to maintain the manual effort until the dosage is completely delivered. With a large volume dosage, it may take an extended period of time (several minutes to an hour or longer) for the dosage reservoir to empty, and it is not practical for a patient to maintain finger pressure for such an extended period of time.

The practical size of the bolus dosage is also limited by the fact that the bolus is infused over a short period of time (from a few seconds or less up to several minutes), and the amount of fluid the body can absorb in such a short time is very limited. For example, clinicians treating post-operative pain following orthopedic surgery with a PCA infusion of local anesthetic agent into the surgical site have observed that even a 5-cc bolus dosage often leaks out of the incisions, depriving the patient of the full anesthetic effect of the medication and potentially inhibiting healing of the incision.

Another problem with currently available disposable PCA devices is that they have a bolus reservoir that fills slowly without any patient input. The problem with this is that if a patient does not need a bolus, the unused medication in the bolus reservoir is wasted. With expensive medications, this waste is not economical, especially with large bolus sizes.

Another problem with those currently available disposable PCA devices that provide basal-bolus infusion is that they have two parallel flow paths, each with their own flow restrictor, and a valve is required immediately downstream of the bolus reservoir. The use of two flow restrictors and the valve add cost and complexity to the mechanism. Also, in devices utilizing a passive check valve (which requires a "cracking pressure" that is somewhat higher than the medication reservoir pressure) the patient has to apply significant additional force to the bolus mechanism in order to open the valve to deliver the bolus.

Another problem with currently available disposable PCA devices is that by placing the flow restrictors proximal to the bolus reservoir, the fluid path volume distal to the flow restrictors is relatively large. Since all segments of the fluid path that are distal to the flow restrictor are primed at the restricted flow rate, these devices take a long time to prime (often in excess of 30-60 minutes). This long priming time is inconvenient for the clinicians setting up the device, and is not a cost-effective use of nursing time (especially if the device is being used in an operating room, where wasted setup time can results in hundreds of dollars worth of lost productivity in room usage).

As previously mentioned, these devices have two parallel flow paths, each with their own flow restrictor. A precision flow restrictor is often the costliest component of the device. A device that requires two flow restrictors for two distinct flow rates may be significantly more costly that a device that needs only one flow restrictor to achieve two distinct flow rates, such as the device described herein.

There exists a demonstrated need for an infusion device that is capable of administering a series of controlled-volume dosages of fluid, and offers the following features and benefits:

The dosage reservoir is able to accommodate a relatively large controlled-volume dosage of 5 to 10 cc's or more, or an even larger dosage volume of 25 to 100 cc's or more, and the device infuses the dosage at a controlled rate over an extended period of time;

The dosage reservoir does not fill with medication unless the user activates the dosage, so that medication waste is minimized;

The device minimizes the number and complexity of components, especially expensive components such as flow restrictors, to keep the cost as low as possible;

The device is easy to setup and priming time is minimized; and

The device is easy for the patient to use, with actuation forces minimized and the need to apply force for an extended period of time eliminated.

SUMMARY OF THE INVENTION

This invention provides an infusion device for delivery of a controlled-volume dosage of a fluid to a patient. The infusion device includes a medication reservoir and a dosage reservoir connected by a first fluid conduit with a one-way valve that allows fluid flow only away from the medication reservoir. A pressure source applies pressure, greater than the medication reservoir pressure, to dispense the fluid from the dosage reservoir through a second fluid conduit leading to a patient connection. From an initial empty state, an actuator temporarily checks the pressure source to enable the dosage reservoir to rapidly fill with a controlled volume of fluid from the medication reservoir. After actuation, a flow restrictor in the second fluid conduit restricts flow from the dosage reservoir to the patient connection.

The infusion device is also capable of administering liquid medication at a continuous basal flow rate, and upon user demand delivering liquid medication at a higher dosage bolus flow rate. The basal flow rate is provided by pressure exerted by the medication reservoir while the dosage reservoir is empty. In contrast, after actuation of the dosage reservoir, the pressure of the dosage reservoir results in the temporary higher bolus flow rate. Thus, two distinct flow rates are achieved with one flow restrictor element.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 5a is a perspective view of the dosage reservoir shown in FIG. 4a in its empty state.

FIG. 5b is a perspective view of the dosage reservoir shown in FIG. 4b with the dosage reservoir filled with fluid.

FIG. 10b is a perspective view of the embodiment of the syringe-style shown in FIG. 10a.

FIG. 11b is a perspective view of the embodiment of the syringe-style shown in FIG. 11a.

DETAILED DESCRIPTION OF THE INVENTION

Figure 1A:
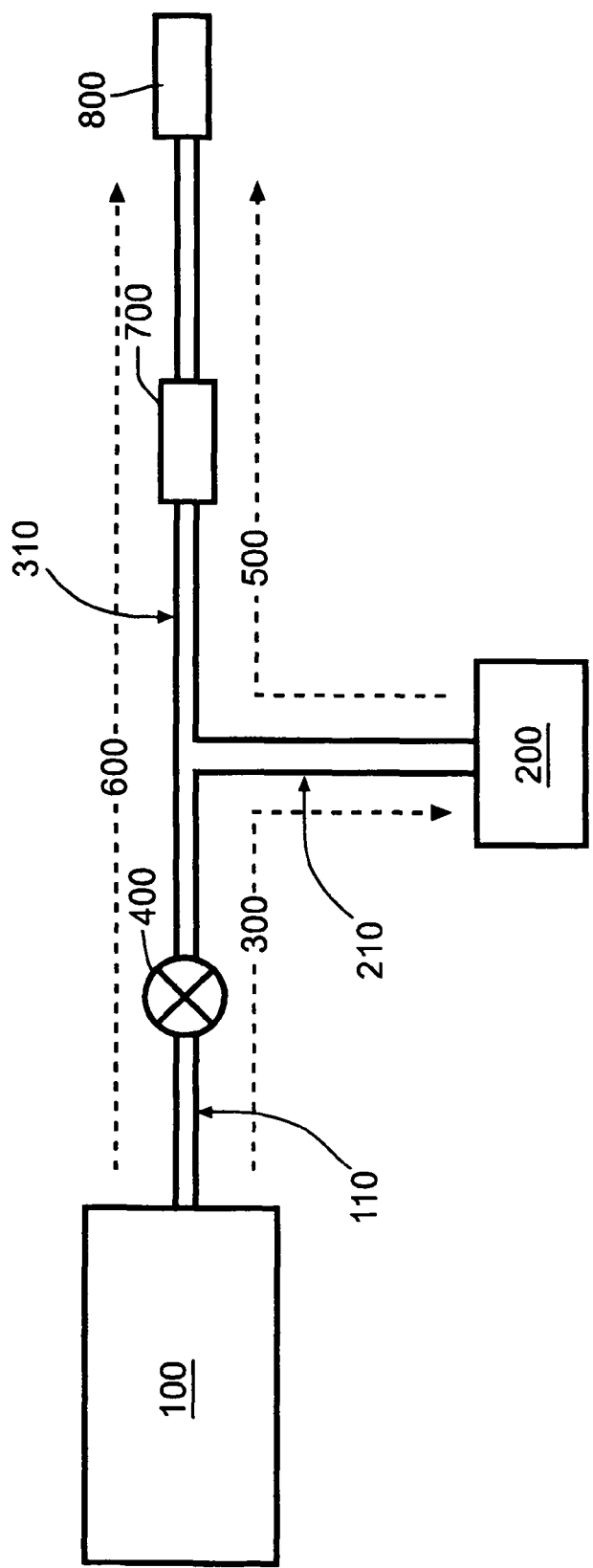
FIG. 1a is a diagram of the "basal-bolus" embodiment of the invention.

FIG. 1a shows a schematic view of the "basal-bolus" embodiment of the invention, providing for administration of a series of controlled-volume dosages of medication or other fluid with a continuous flow of fluid between dosages. The device includes a medication reservoir 100 that holds medication or other fluid under substantially constant pressure (the medication reservoir pressure, $P_m$). When the user actuates the controlled-volume dosage, the medication reservoir pressure causes fluid to be expelled from the medication reservoir 100, and to flow through the first fluid flow path 300 through the source conduit 110 and dosage conduit 210 into the controlled-volume dosage reservoir 200. When the dosage reservoir 200 is filled (as illustrated in FIG. 1c), the fluid within the dosage reservoir 200 is pressurized to a higher substantially constant pressure (the dosage reservoir pressure, $P_d$, which is not necessarily constant), which is greater than the medication reservoir pressure, the ratio $P_m:P_d$ being predetermined and controlled to provide the desired infusion flow characteristics. A valve 400 is disposed within the first fluid flow path 300, between the medication reservoir 100 and the dosage reservoir 200. The valve 400 allows fluid flow in the downstream direction from the medication reservoir 100 toward the dosage reservoir 200 and the distal end 800, but prevents flow in the opposite direction back into the medication reservoir, and thereby acts to prevent fluid flow from the higher-pressure dosage reservoir 200 back into the lower-pressure medication reservoir 100. The dosage reservoir pressure causes fluid to be expelled from the dosage reservoir 200; the valve 400 prevents this fluid from flowing back into the medication reservoir 100, therefore the fluid flows through the second fluid flow path 500, through optional dosage conduit 210, through delivery conduit 310, through the flow restrictor element 700, and out the distal end 800 of the device. The flow restrictor element 700 controls the infusion rate at which the fluid flows from the dosage reservoir 200 out through the distal end 800, the flow-restricting properties of the flow restrictor element 700 being predetermined and controlled to, in conjunction with the dosage reservoir pressure, provide the desired infusion flow characteristics for the controlled-volume dosage.

In the periods between controlled-volume dosages, when there is no flow into or out of the dosage reservoir 200, the medication reservoir pressure causes fluid to be expelled from the medication reservoir 100, and to flow through the third fluid flow path 600, through the flow restrictor 700, and out the distal end 800 of the device. The flow restrictor element 700 controls the infusion rate at which the fluid flows from the medication reservoir 100 out through the distal end 800, the flow-restricting properties of the flow restrictor element 700 being predetermined and controlled to, in conjunction with the medication reservoir pressure, provide the desired infusion flow characteristics for the continuous fluid flow between controlled-volume dosages.

Located on the dosage reservoir 200, there may be indications or markings denoting the volume of fluid delivered or remaining in the reservoir. Additionally these indications could denote the amount of time the dosage has been administered or time remaining of the dosage delivery.

Figure 1B:
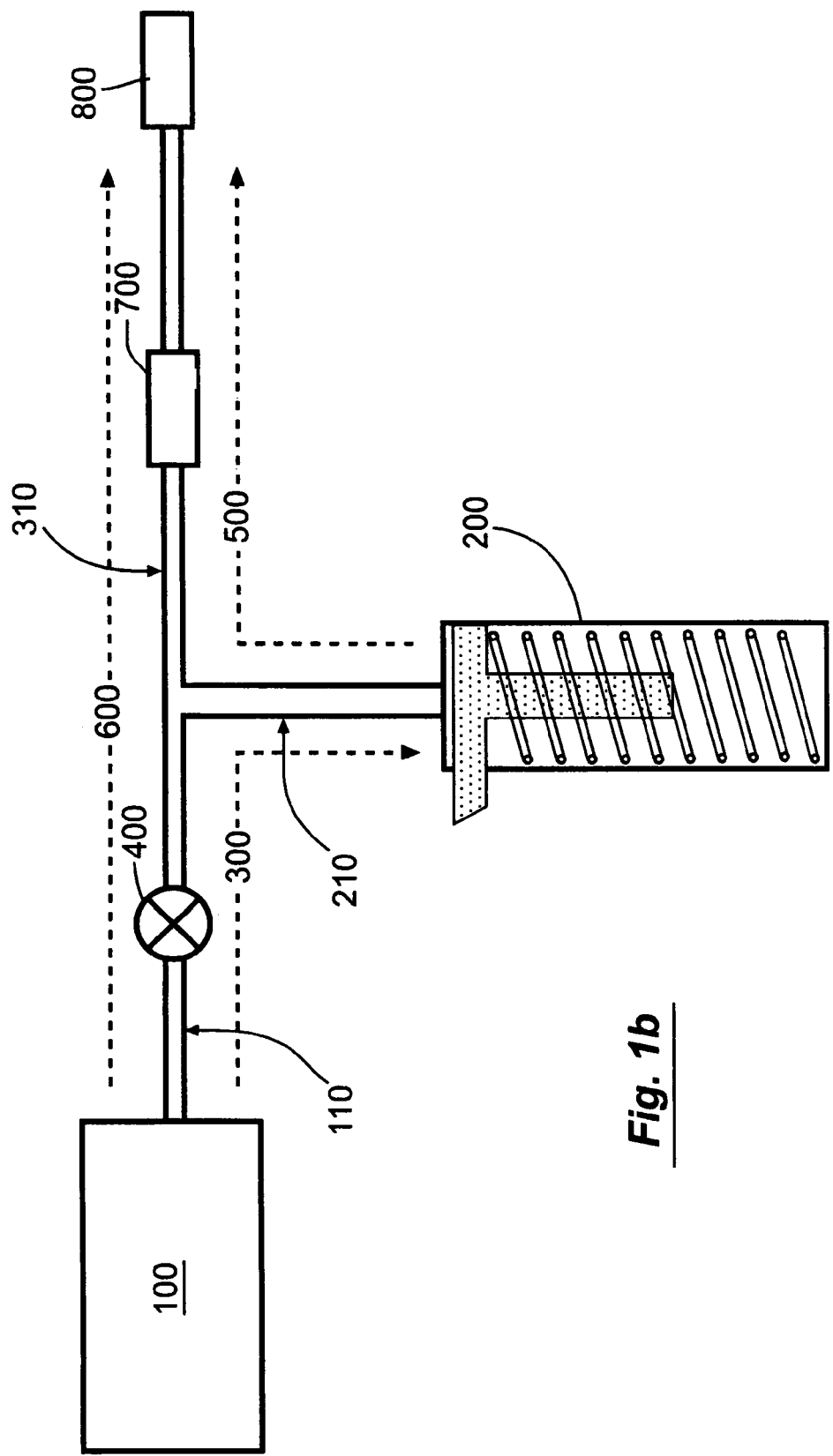
FIG. 1b is a diagram corresponding to FIG. 1a with the dosage reservoir 200 in its passive state with an empty reservoir.
Figure 1C:
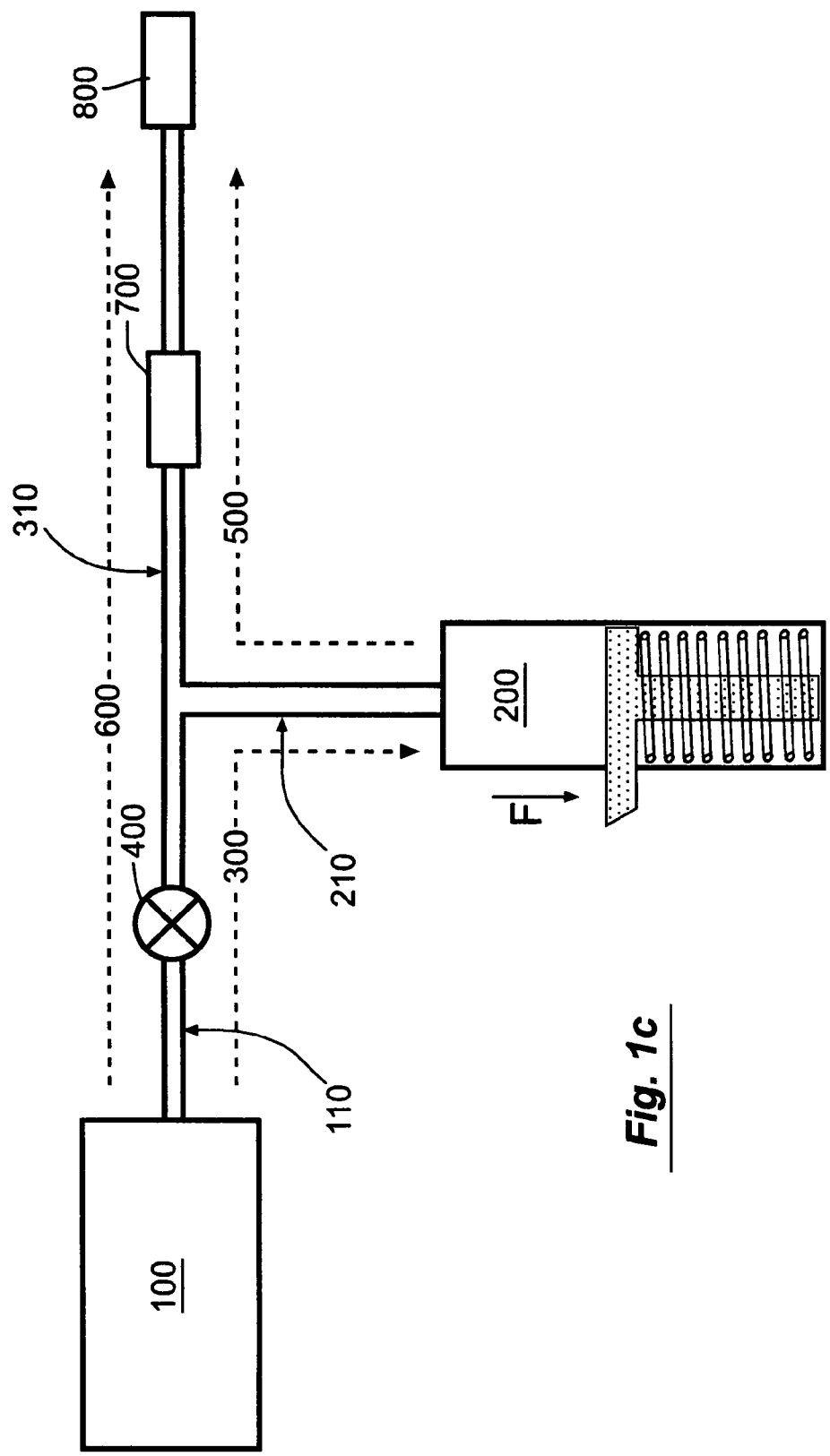
FIG. 1c is a diagram corresponding to FIGS. 1a and 1b with the dosage reservoir 200 being filled.

FIG. 1b illustrates the dosage reservoir 200 in its biased position (passive state), with an empty reservoir. In this position, the dosage reservoir does not have any effect on the fluid pressure. FIG. 1c illustrates dosage reservoir being actuated. The reservoir is constructed such that it is enabled to open no more than the controlled volume dosage. To actuate the dosage reservoir 200, the user exerts a force F to open the reservoir. This allows fluid to flow in to the dosage reservoir 200, from the medication reservoir 100. Once the dosage reservoir 200 is full, and the user releases the actuator, the dosage reservoir exerts a controlled pressure $P_d$, which is higher than the medication reservoir pressure.

Figure 1D:
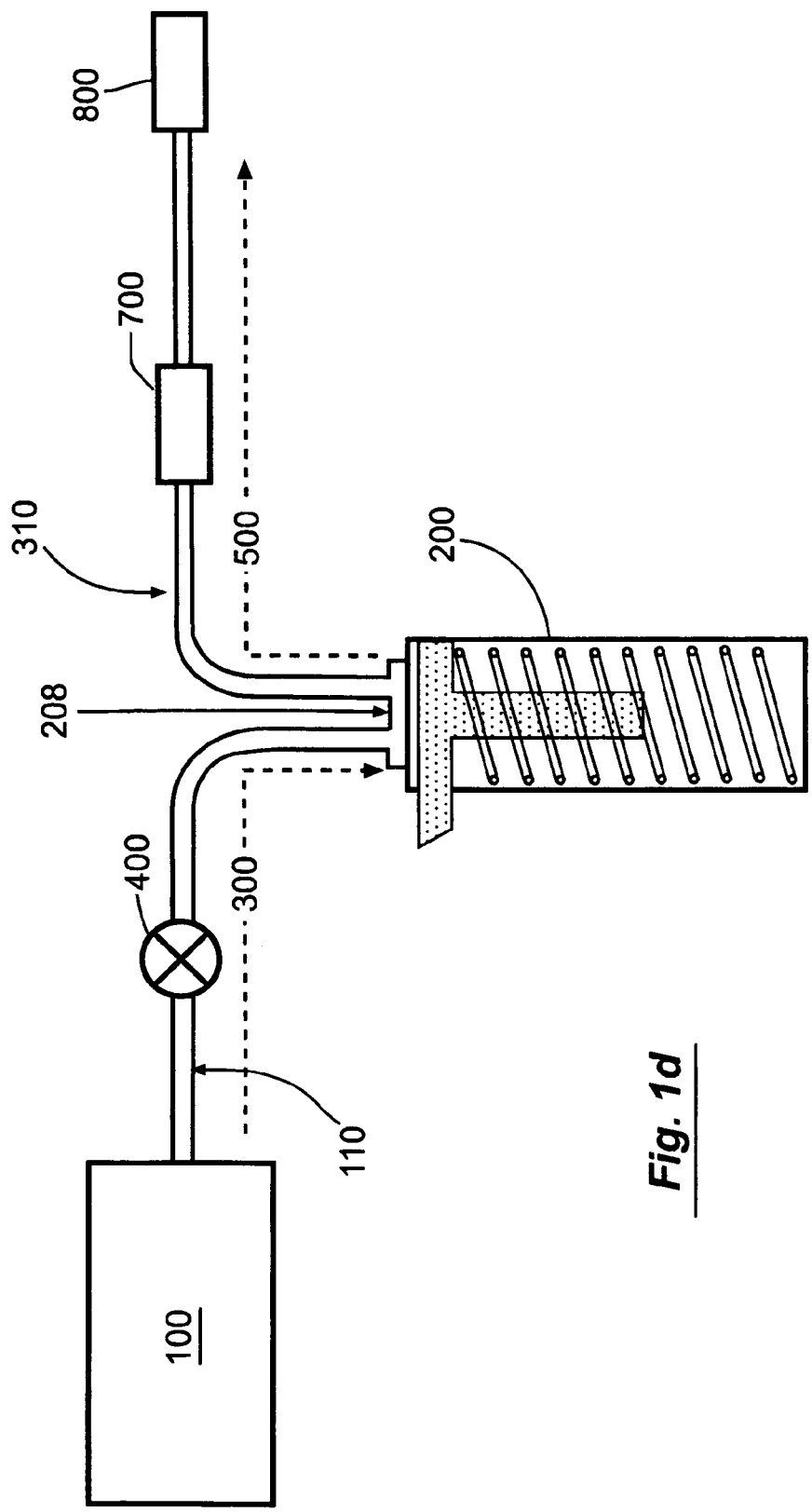
FIG. 1d and 1e are diagrams of another embodiment similar to FIGS. 1a-1c, but without a separate dosage conduit 210.
Figure 1E:
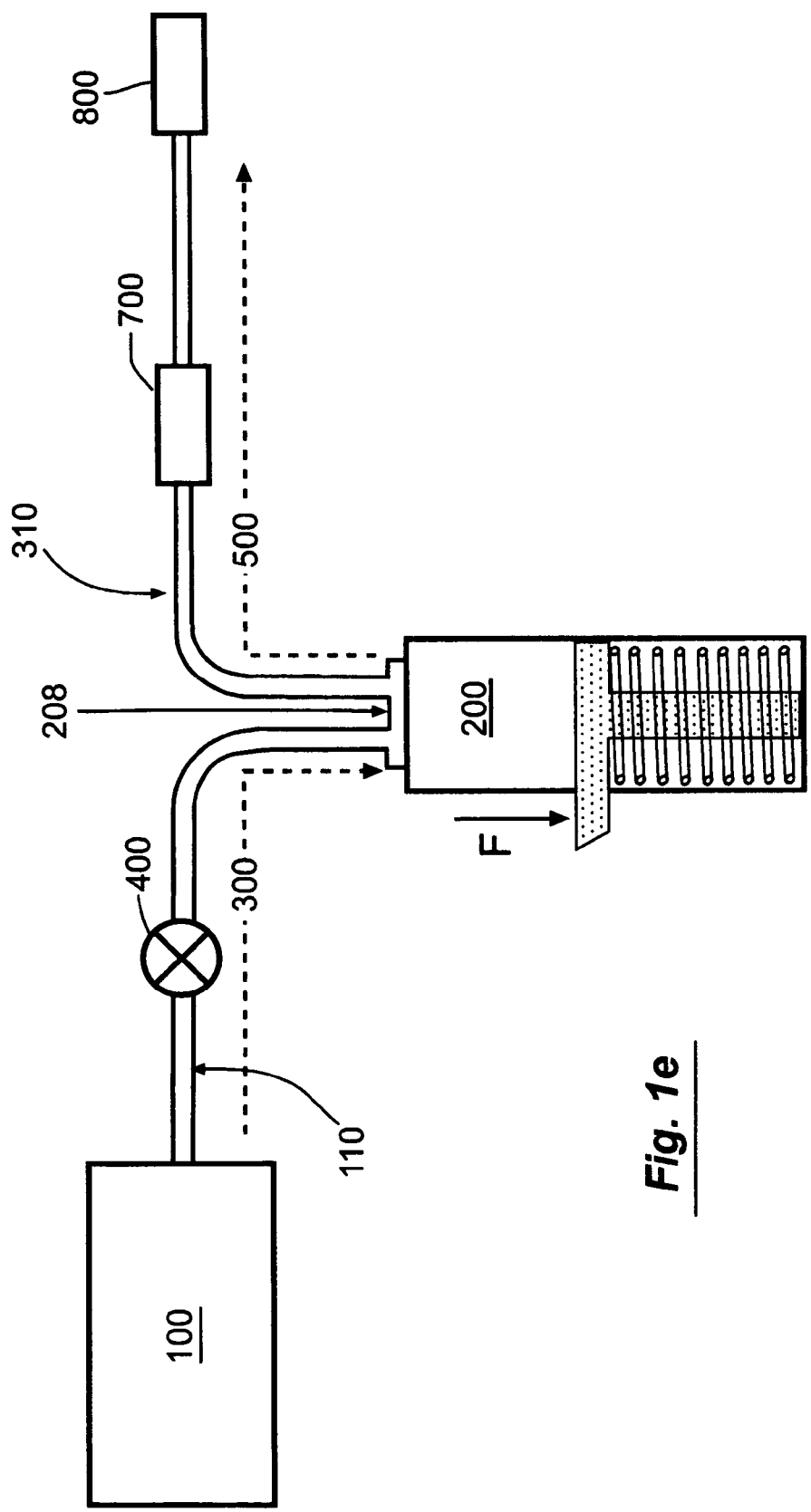

FIG. 1d and 1e both illustrate the opening and closing of the dosage reservoir 200, but there is no dosage conduit 210. In this configuration, fluid flows from the medication reservoir 100 directly into dosage reservoir 200 through the source conduit 110 and check valve 400. When the dosage reservoir 200 is empty, as shown in FIG. 1d, a continuous flow of fluid bypasses the dosage reservoir by means of the bypass flow region 208. As shown in FIG. 1e, after the dosage reservoir 200 has been actuated, there is flow only in delivery conduit 310. The bypass flow region 208 is a region of the dosage reservoir in which fluid enters via source conduit 110 and exits via delivery conduit 310. However, it is not necessary that the bypass flow region 208 be part of the dosage reservoir. It could be a separate tube that connects source conduit 110 and delivery conduit 310, in parallel with dosage reservoir 200.

Figure 2:
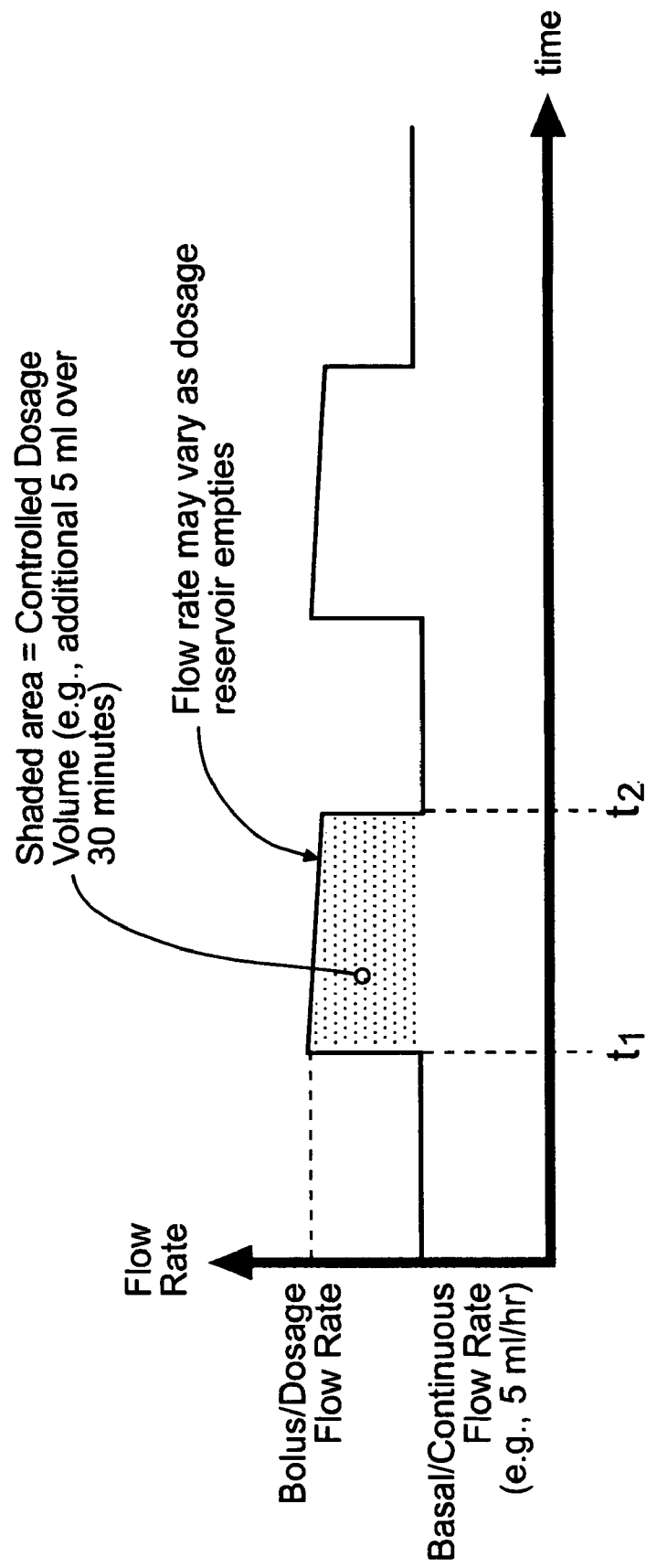
FIG. 2 is a graph of the resulting flow profile from the infusion device.

The flow rate profile is shown in FIG. 2. With a substantially constant pressure, $P_m$, from the medication reservoir 100, there is a substantially constant basal flow rate delivered to the patient at the distal end 800. This is exhibited in FIG. 2 at times before $t_1$. The time $t_1$ is defined as the moment that the user completes actuation of the dosage reservoir. Just after $t_1$, the dosage reservoir is full and at a higher pressure $P_d$. The time $t_2$ is defined as the moment after $t_1$ that the dosage reservoir becomes empty. In the period of time between to and $t_2$, the dosage reservoir pressurizes the fluid upstream of the flow restrictor element 700, which causes the flow rate to increase from a basal flow rate to a higher bolus flow rate. As soon as the dosage reservoir had delivered all its contents and becomes empty at $t_2$, the fluid pressure drops back to $P_m$ and the flow rate drops back to the basal flow rate. The shaded area of the graph illustrates the controlled volume dosage. The user may deliver a multiple of dosages, thus creating a flow profile as illustrated in FIG. 2.

Medication Reservoir 100. The medication reservoir 100 may utilize any of a number of known technologies for providing a reservoir capable of receiving fluid, applying a known pressure to the fluid, storing the fluid under pressure, and dispensing the fluid under pressure. Examples of existing devices providing an appropriate medication reservoir that would be suitable for use in the present invention include but are not limited to the Beeline MotIV (spring-powered syringe-style pump, U.S. Design Pat. No. 453,830), the Out-Bound DSI (vacuum-powered syringe-style pump, U.S. Pat.

No. 5,135,500), and the Accufuser (balloon-style pump, U.S. Pat. No. 6,024,724), all sold by McKinley Medical.

The system requires a fill port by which fluid is introduced into the medication reservoir 100. This fill port may take the form of a Luer connection, septum (for piercing with a needle or spike), or other appropriate connection. In this embodiment, the fill port is comprised of a female Luer-lock connection and a one-way valve; the male Luer termination of a syringe or filling pump is connected to the female Luer connection of the fill port; fluid is transferred under pressure from the syringe or filling pump into the medication reservoir, the transfer pressure being sufficient to overcome the medication reservoir pressure; when the syringe or filling pump is disconnected from the fill port, the one-way valve acts to prevent the fluid in the medication reservoir from flowing back out of the fill port. The fill port may be located within the medication reservoir 100, or may be disposed within the first fluid flow path 300 between the medication reservoir 100 and the valve 400.

The medication reservoir 100 is sized to hold enough fluid as to provide for the necessary number of controlled-volume dosages and continuous flow of fluid between dosages, as required by the specific therapy for which the device is selected. For example: a 10-mL reservoir would provide adequate capacity for a therapy requiring 0.02-mL/hr continuous flow with 0.2-mL controlled volume dosages once every four hours for approximately 6 days; a 100-mL reservoir would provide adequate capacity for a therapy requiring 2-mL/hr continuous flow with 2-mL controlled volume dosages once an hour for approximately 1 day; a 350-mL reservoir would provide adequate capacity for a therapy requiring 5-mL/hr continuous flow with 5-mL controlled volume dosages once every 2 hours for approximately 2 days; a 1000-mL reservoir would provide adequate capacity for a therapy requiring 2-mL/hr continuous flow with 50-mL controlled volume dosages once every 8 hours for approximately 5 days of therapy.

The medication reservoir 100 generates sufficient pressure to drive fluid through the system and to overcome any backpressure at the infusion site (e.g., a small-bore infusion catheter distal to the device, or pressure within the patient's vasculatory system). Typical infusion applications require a pressure of at least 3-4 psi; more commonly (such as in the Beeline, OutBound, and Accufuser products referenced above), the medication reservoir generates pressures in the 5-15 psi range; higher pressures of 20-40 psi or even higher are desirable in certain applications.

Dosage Reservoir 200. The dosage reservoir 200 includes a pressure-generating mechanism or pressure source that generates a higher fluid pressure than the medication reservoir 100. In addition, the dosage reservoir 200 includes an actuator for temporarily checking the pressure source, thereby reducing or eliminating the pressure within the dosage reservoir, creating a pressure drop from the medication reservoir 100 across the first fluid flow path 300, and resulting in flow of fluid to fill the dosage reservoir 200. After the actuator has been used to fill the dosage reservoir 200, The pressure source generates higher pressure within the dosage reservoir 200 than the medication reservoir 100, so that fluid flowing under pressure from the dosage reservoir 200 through the flow restrictor element 700 flows at a faster rate than fluid flowing under pressure from the medication reservoir 100 through the same flow restrictor element 700. The ratio between dosage reservoir pressure and medication reservoir pressure determines the ratio between the infusion rate of the controlled-volume dosages and the infusion rate of the continuous flow between the controlled volume dosages. For example: if the dosage reservoir 200 generates 12 psi of fluid pressure and the medication reservoir 100 generates 6 psi of fluid pressure, for a pressure ratio of two, the controlled-volume dosages will infuse at twice the infusion rate as the continuous basal flow between the controlled-volume dosages; if the pressure ratio is 1.5, the controlled-volume dosages will infuse 50% faster than the continuous flow; if the pressure ratio is 4, the controlled-volume dosages will infuse 4 times as fast the continuous flow.

The dosage reservoir 200 may utilize any of a number of known technologies for providing a reservoir capable of receiving fluid, applying a known pressure to the fluid, storing the fluid under pressure, and dispensing the fluid under pressure, provided that the mechanism for applying pressure to the fluid can be selectively and temporarily removed by the user by opening reservoir by temporarily applying force, F. Examples of appropriate reservoirs that would be suitable for use as the dosage reservoir in the present invention include but are not limited to: a syringe-style reservoir pressurized by a spring as the pressure source (similar to the medication reservoir in the above-referenced Beeline MotIV pump) or by a vacuum mechanism (similar to the medication reservoir in the above-referenced OutBound DSI pump). For example, the actuator can be a slide, lever, or other mechanism to manually compress the spring or expand the vacuum chamber, thereby temporarily checking the pressurizing force from the syringe plunger or actively drawing the syringe plunger back and allowing the syringe to fill. Alternatively, a bag-style reservoir (similar to the bolus dose reservoir in the above-referenced Accufuser pump) can be pressurized by a spring. Here again, an actuator (e.g., a slide, lever, or other mechanism) enables the user to manually compress the spring, thereby checking or retracting the pressurizing force from the bag and allowing the bag to fill. In another embodiment, a bellows-style reservoir is pressurized by any appropriate pressure source (e.g., a spring or compressed gas). An actuator enables the user to manually hold the bellows open against the pressurizing mechanism and allows the bellows to fill. Similarly, a rolling-diaphragm-style reservoir can be designed with a force-applying rod bearing on the diaphragm and energized by any appropriate mechanism (such as a spring, stretched elastic member, or pneumatic pressure), with a slide, lever, or other mechanism such that the user can manually draw back the force-applying rod, thereby removing the pressurizing force from the diaphragm and allowing the reservoir to fill.

The dosage reservoir 200 is sized to hold enough fluid for one controlled-volume dosage, as required by the specific therapy for which the device is selected. For example: a 0.2- or 0.3-mL dosage reservoir would provide the typical dosage volume for tocolytic therapy; a 0.5- or 1-mL dosage reservoir would provide the typical dosage volume for IV pain management applications; a 2-, 5-, or 10-mL dosage reservoir would provide the typical dosage volume for nerve block pain management applications; a 10-, 25-, 50-, or 100-mL dosage reservoir would provide the typical dosage volume for IV antibiotic applications.

The dosage reservoir volume may be fixed during manufacturing, or may be user-selectable. Examples of a user-selectable mechanism for the controlled-volume dosage reservoir include but are not limited to: a screw-mounted stop that limits the travel of the plunger in a syringe-style dosage reservoir, such that the user can dial the screw to locate the stop for the desired volume; a rigid, movable plate bearing against one side of the flexible bag in a bag-style dosage reservoir, with a sliding wedge behind the rigid plate that limits the travel of the rigid plate, such that the user can slide the wedge in or out to locate the travel limit of the rigid plate for the desired volume. Optional graduation indicia on the external housing match up to the travel of the actuator (e.g., slide or lever), so the user can visually detect how far the dosage reservoir has opened and selectively limit the travel of the actuator to achieve the desired volume.

First Fluid Flow Path 300. In the embodiment shown in FIGS. 1a-1e and 2, the first fluid flow path 300 can take the form of a flexible tube, such as a length of medical-grade PVC tubing or other similar tubing commonly used for infusion sets. In other embodiments, the first fluid path 300 may take the form of a rigid molded or machined channel (for instance, where the medication reservoir 100, dosage reservoir 200, and first fluid path 300 are all formed within an integrated housing or block of material), or a flexible channel (for instance, where the medication reservoir 100 or the dosage reservoir 200 are formed as a substantially flat bag by welding together two flexible sheets, with the first fluid flow path 300 also formed as a welded region between the two flexible sheets).

The first fluid flow path 300 may be comprised of one integral unit, such as a continuous length of tubing or continuous molded channel. Alternately, the first fluid flow path 300 may be comprised of several members joined together. In the this embodiment, the first fluid flow path 300 is comprised of: a length of tubing (the source conduit 110) between the medication reservoir 100 and the valve 400, a molded flow path through the valve 400 component, another length of tubing (more source conduit 110) between the valve 400 and a 3-leg adapter component 350, a molded flow path through the 3-leg adapter component 350, and another length of tubing between the 3-leg adapter component 350 and the dosage reservoir 200. A snap clamp 111 may be placed anywhere over source conduit 110 to stop the flow of fluid from the medication reservoir. The snap clamp 111 may be a standard commercial snap clamp, or may take the form of a slide clamp, valve, or any means to stop the fluid flow.

The first fluid flow path 300 may be permanently connected to the medication reservoir 100 and the dosage reservoir 200, such as a length or lengths of tubing bonded on each end. Alternately, the first fluid flow path 300 may be a removably-connected member of the system, such as a length or lengths of tubing terminating in Luer connectors, with mating Luer connectors on the medication reservoir 100, the valve 400, or the dosage reservoir 200.

Valve 400. The sole purpose of the valve 400 is to prevent fluid flow from the dosage reservoir 200 back into the medication reservoir 100. The valve 400 is not required to prevent continuous fluid flow from the medication reservoir 100 into the dosage reservoir 200, because this is prevented by the positive pressure differential between the two reservoirs (until the user actuates the mechanism to remove the dosage reservoir pressure). In the embodiment of the device depicted schematically in FIG. 1, the valve 400 is required to allow fluid flow from the medication reservoir 100 through the third fluid flow path 600. In this embodiment of the device, the valve 400 is disposed within the first fluid flow path 300 such that the valve is normally open to allow flow out of the medication reservoir 100 and on to distal points in the fluid flow path, and passively closes to substantially prevent flow from distal points in the fluid flow path back into the medication reservoir 100. The valve 400 may utilize any of a number of known technologies for providing a normally-open one-way check valve, such as a duckbill-style valve, ball-style valve, disc-style valve, or similar.

Second Fluid Flow Path 500. The second fluid flow path 500 can take the form of a flexible tube, such as a length of medical-grade PVC tubing or other similar tubing commonly used for infusion sets. In other embodiments, the second fluid flow path 500 may take the form of a rigid molded or machined channel (for instance, where the dosage reservoir 200, second fluid flow path 500, and distal end 800 are all formed within an integrated housing or block of material), or a flexible channel (for instance, where the dosage reservoir 200 is formed as a substantially flat bag by welding together two flexible sheets, with the second fluid flow path 500 also formed as a welded region between the two flexible sheets). A slide clamp 311 may be placed anywhere over delivery conduit 310 to stop the flow of fluid from either of the two reservoirs. It may be a standard commercially available slide clamp, a snap clamp, valve, or any means to stop the fluid flow.

The second fluid flow path 500 may be comprised of one integral unit, such as a continuous length of tubing or continuous molded channel. Alternately, the second fluid flow path 500 may be comprised of several members joined together. The second fluid flow path 500 includes a length of tubing between the dosage reservoir 200 and a 3-leg adapter component 350, a molded flow path through the 3-leg adapter component 350, another length of tubing between the 3-leg adapter component 350 and an air-eliminating filter component 710, a molded flow path through the air-eliminating filter component 710, a last length of tubing between the air-eliminating filter component 710 and the distal end 800 (the last length of tubing including the flow restrictor element 700), and a molded flow path through the distal end 800.

The second fluid flow path 500 may share common elements with the first fluid flow path 300. For example, in the above descriptions, the length of tubing between the dosage reservoir 200 and the 3-leg adapter component 350 is an element of both the first fluid flow path 300 and the second fluid flow path 500, depending upon which direction the fluid is flowing through the length of tubing (when fluid is flowing into the dosage reservoir 200, the length of tubing is part of the first fluid flow path 300; when fluid is flowing out of the dosage reservoir 200, the length of tubing is part of the second fluid flow path 500). The second fluid flow path 500 may be permanently connected to the dosage reservoir 200. Alternately, the second fluid flow path 500 may be a removably-connected member of the system, such as a length of tubing with a proximal Luer connector, with a mating Luer connector on the dosage reservoir 200.

Third Fluid Flow Path 600. The third fluid flow path 600 can take the form of a flexible tube, such as a length of medical-grade PVC tubing or other similar tubing commonly used for infusion sets. In alternate embodiments, the third fluid flow path 600 may take the form of a rigid molded or machined channel (for instance, where the medication reservoir 100, third fluid flow path 600, and distal end 800 are all formed within an integrated housing or block of material), or a flexible channel (for instance, where the medication reservoir 100 and dosage reservoir 200 are formed as substantially flat bags by welding together two flexible sheets, with the third fluid flow path 600 also formed as a welded region between the two flexible sheets).

The third fluid flow path 600 may be comprised of one integral unit, such as a continuous length of tubing or continuous molded channel. Alternately, the third fluid flow path 600 may be comprised of several members joined together. Preferably, the third fluid flow path 600 includes a length of tubing between the medication reservoir 100 and the valve 400, a molded flow path through the valve 400 component, another length of tubing between the valve 400 and a 3-leg adapter component 350, a molded flow path through the 3-leg adapter component 350, another length of tubing between the 3-leg adapter component 350 and an air-eliminating filter component 710, a molded flow path through the air-eliminating filter component 710, a last length of tubing between the air-eliminating filter component 710 and the distal end 800 (the last length of tubing comprising the flow restrictor element 700), and a molded flow path through the distal end 800.

The third fluid flow path 600 may share common elements with the first fluid flow path 300 and the second fluid flow path 500. For example, in the above descriptions, all elements of the first fluid flow path 300 up to the 3-leg adapter component 350, and all elements of the second fluid flow path 500 below the 3-leg adapter component 350, are also elements of the third fluid flow path 600, depending upon whether a controlled-volume dosage has been actuated (when the controlled-volume dosage is filling or infusing, the fluid path elements are making up the first or second fluid flow paths; when the continuous flow between controlled-volume dosages is flowing, the fluid path elements are making up the third fluid flow path). As described for the first and second fluid flow paths, the third fluid flow path 600 may be permanently connected to the system or may be a removably-connected member of the system.

Flow Restrictor Element 700. The flow restrictor element 700 must provide a known flow restriction such that the fluid flow rate through the flow restrictor element 700 is proportional to the pressure drop across the flow restrictor element 700. Examples of appropriate flow restrictors that would be suitable for use as the flow restrictor element 700 in the present invention include but are not limited to: a thin-plate flow orifice with controlled plate thickness, orifice diameter, and edge sharpness; a length of capillary tube with controlled inside diameter and length; a porous membrane or similar porous barrier with controlled pore size and wetted area. These types of flow restrictors function under the principle of providing a resistance to fluid flow such that flow rate through the flow restrictor is substantially proportional to the pressure differential across the flow restrictor; by manipulating the controlled parameters of the flow restrictor during manufacturing, the flow restrictor element 700 can be matched to the pre-determined medication reservoir pressure and dosage reservoir pressure such that the desired infusion flow rate parameters are achieved.

It is often desired to place an air-eliminating filter 710 just upstream of the flow restrictor element 700. The air-eliminating filter 710 may be of a standard commercially-available variety, placed inline with the delivery conduit 310. However, it may also be integrated into the flow restrictor 700, or anyplace along the delivery conduit 310, as long as it is upstream of the flow restrictor element 700.

Distal end 800. The distal end 800 of the device provides a fluid connection between the device and the infusion site. For example, the distal end 800 can take the form of a Luer-lock connector. Alternately, the distal end 800 can include a needle, an infusion catheter, or other appropriate connector. All of these should be interpreted generically as various types of "patient connections".

Figure 3:
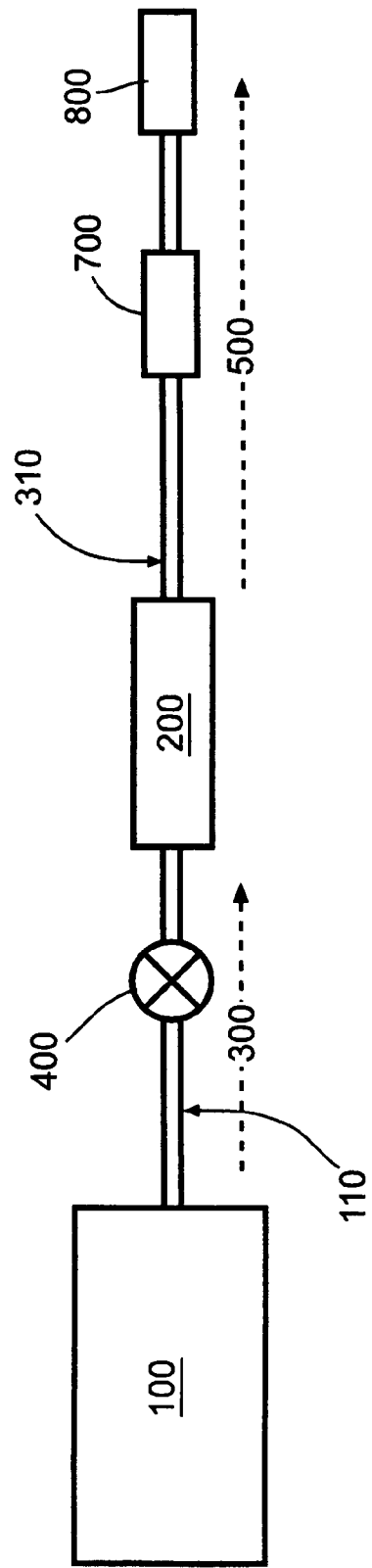
FIG. 3 is a diagram of the "bolus-only" embodiment of the invention.

FIG. 3 shows a schematic view of a "bolus-only" embodiment of the invention, providing only for administration of a series of controlled-volume dosages of medication or other fluid, with no provision for a continuous flow of fluid between dosages. The device comprises a medication reservoir 100 that holds medication or other fluid under pressure (the medication reservoir pressure), and a dosage reservoir 200 that, when filled, holds the medication or other fluid under substantially constant pressure (the dosage reservoir pressure), which is greater than the medication reservoir pressure. The medication reservoir 100 and the dosage reservoir 200 are connected in fluid communication by the first fluid flow path 300.

A valve 400 is disposed within the first fluid flow path 300, between the medication reservoir 100 and the dosage reservoir 200. When the user actuates a controlled-volume dosage, the pressure drop between the medication reservoir and the dosage reservoir causes fluid to be expelled from the medication reservoir 100, and to flow through the first fluid flow path 300 into the controlled-volume dosage reservoir 200, thereby filling the dosage reservoir 200. The user actuates a controlled-volume dosage by selectively and temporarily removing the pressure source from the dosage reservoir 200, as described in the detailed description of the embodiment of the device depicted schematically in FIG. 1. If the dosage reservoir 200 is configured so as to prevent any bypass flow when the reservoir is empty, the valve 400 need only serve as a check valve, as described in the detailed description of the embodiment of the device depicted schematically in FIG. 1. If the dosage reservoir 200 allows some bypass flow when the reservoir is empty, then the valve 400 must act as a normally-closed valve preventing fluid flow out of the medication reservoir 100 except when opened by the user. To accomplish this function, the valve 400 may utilize any of a number of known technologies for providing a valve that is closed except when actuated by the user, such as a pinch-style valve, stopcock-style valve, or similar.

The remaining details of the embodiment of the device depicted schematically in FIG. 3 are the same as discussed in detail for FIG. 1, with the exception that this embodiment of the device does not provide the third fluid flow path 600 (i.e., no provision for flow that bypasses the dosage reservoir).

Another embodiment of a "bolus-only" design may be configured with an un-pressurized medication reservoir. This embodiment is identical to the embodiment described above in FIG. 3, with the following exceptions: (a) the medication reservoir 100 is at ambient pressure; and (b) the user actuates a controlled-volume dosage by selectively and temporarily removing the pressure source from the dosage reservoir 200, while simultaneously forcing the reservoir open. By forcing the reservoir open, this creates a vacuum in the chamber. Since the medication reservoir 100 is at ambient pressure, fluid flows toward dosage reservoir 200, at a lower pressure.

Figure 4A:
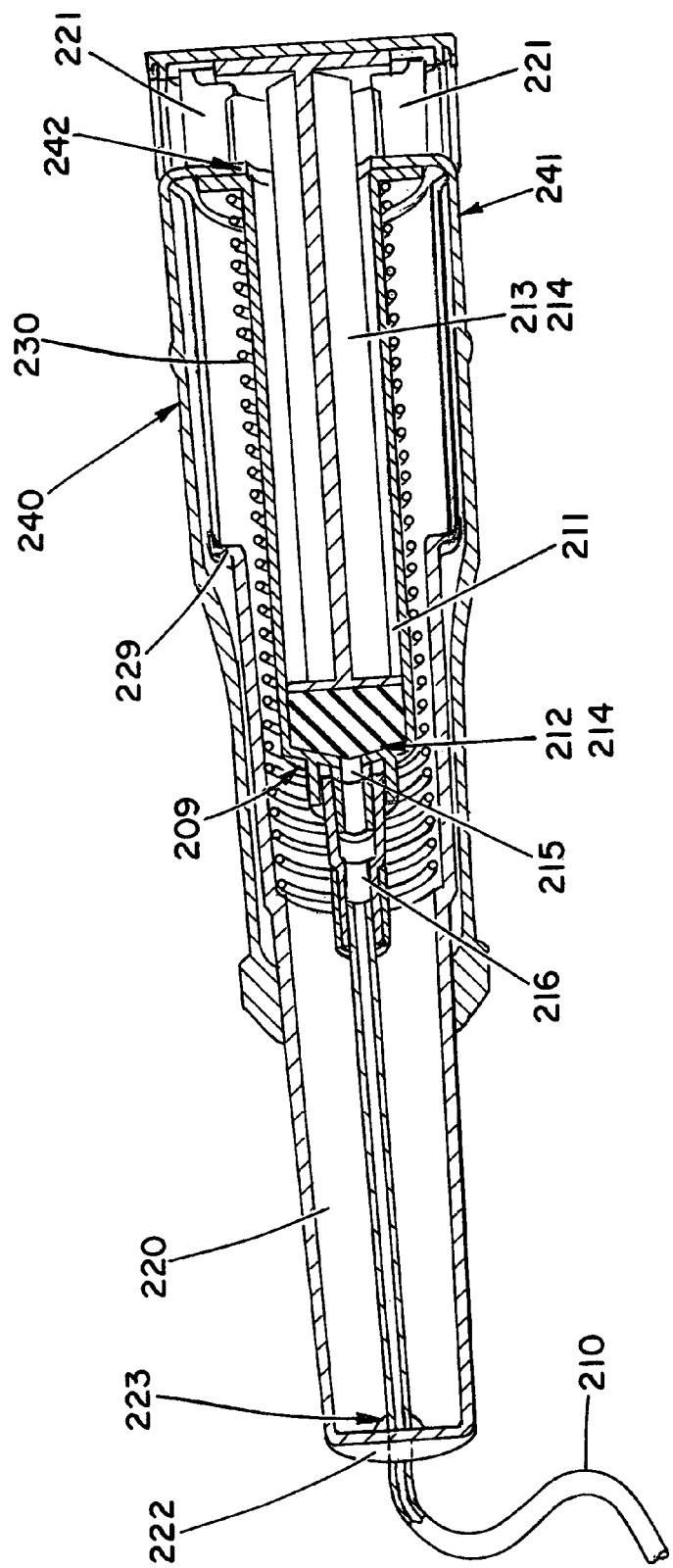
FIG. 4a is a cross-sectional view of a syringe-style dosage reservoir in an empty state.
Figure 4B:
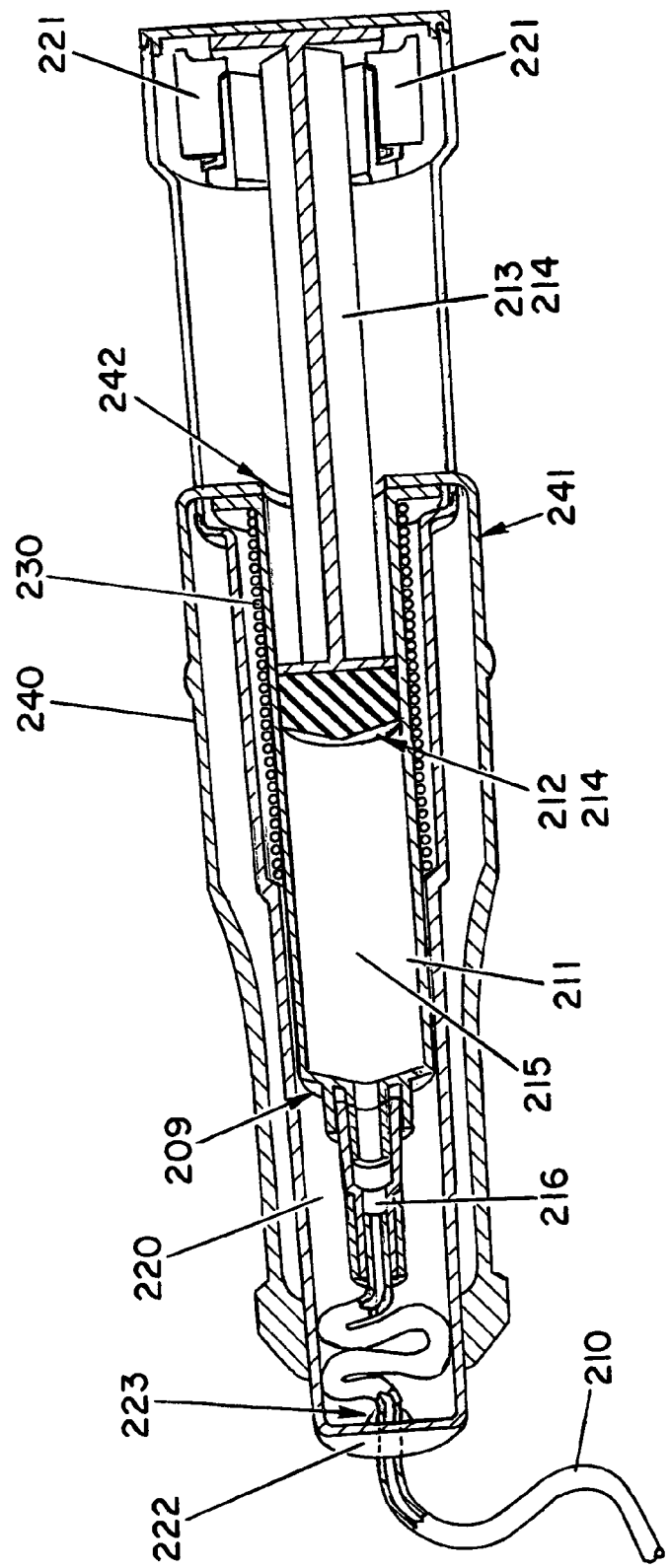
FIG. 4b is a cross-sectional view of the syringe-style dosage reservoir filled with fluid.
Figure 6:
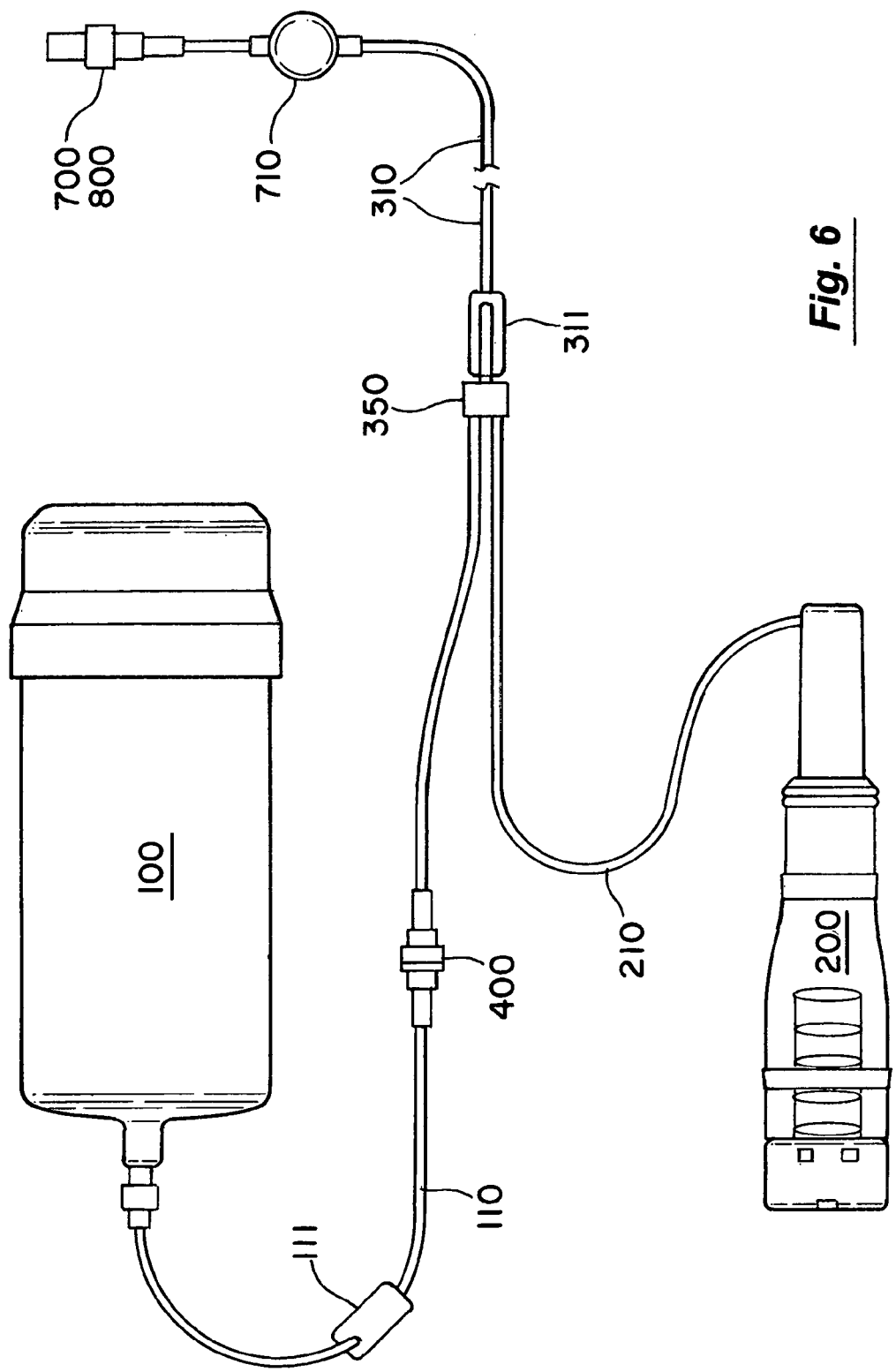
FIG. 6 is a diagram illustrating the overall interconnection of components, including the medication reservoir 100, dosage reservoir 200, three-way adapter 350, check valve 400, and flow restrictor 700.

FIGS. 4a and 4b show cross-sectional views of one of the many potential physical embodiments of the dosage reservoir 200 that would be appropriate for use in the invention as depicted schematically in FIGS. 1 and 3. This particular embodiment of the dosage reservoir 200 incorporates a syringe pressurized with a spring and held inside a housing with a slider mechanism for selectively removing the spring force from the syringe plunger. FIGS. 5a and 5b illustrate the device without the internal mechanisms visible. See FIG. 6 for a diagram of this particular embodiment, as presently manufactured. The dosage reservoir 200 depicted in FIGS. 4a and 4b is comprised of a syringe 209 held inside a housing 220. A spring 230 pressurizes the syringe, and a slider 240 allows the user to selectively and temporarily remove the spring force to de-pressurize the syringe 209. This de-pressurization of the syringe 209 allows the fluid holding chamber portion 215 of the dosage reservoir 200 to fill. The user depressurizes the syringe 209 by grasping the slider 240, pressing the end 222 of the housing 220 against a surface (such as a table top, bed, chair, or the user's body), and sliding the slider 240 in an axial motion with respect to the housing 220 (toward the surface).

Preferably, the syringe is typical of standard syringes commonly used in medical practice and includes a syringe barrel 211, a plunger seal 212 and a plunger rod 213 together forming a syringe plunger 214. The syringe plunger 214 is slidably disposed inside of the syringe barrel 211 to form a fluid-holding chamber 215, with a fluid conduit 216 to provide for ingress and egress of fluid into and out of the fluid-holding chamber 215. Optionally, the syringe may have graduation marks on the syringe barrel 211, as is typical of standard syringes. FIGS. 4a and 4b depict a length of dosage conduit 210 connected to the fluid conduit 216 portion of the syringe 209. This dosage conduit 210, made from flexible tubing, provides a connection between the dosage reservoir 200 and the rest of the device, and is part of the first and second fluid paths discussed and illustrated in FIGS. 1a-1c and FIG. 3.

Figure 4C:
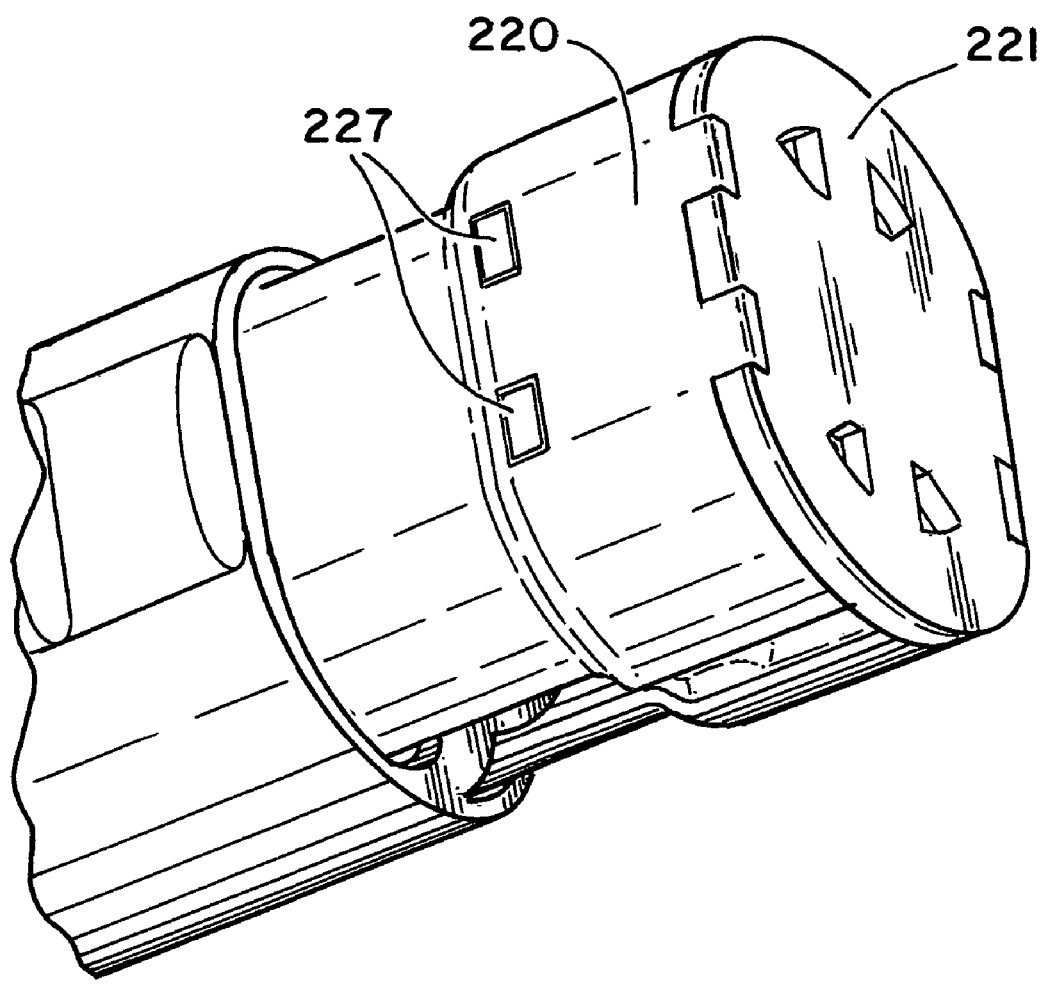
FIG. 4c is a detail perspective view of the end of the syringe housing 220 showing the cap 221 that held in place to the end of the housing 220 with snap engagement feature 227.
Figure 4D:
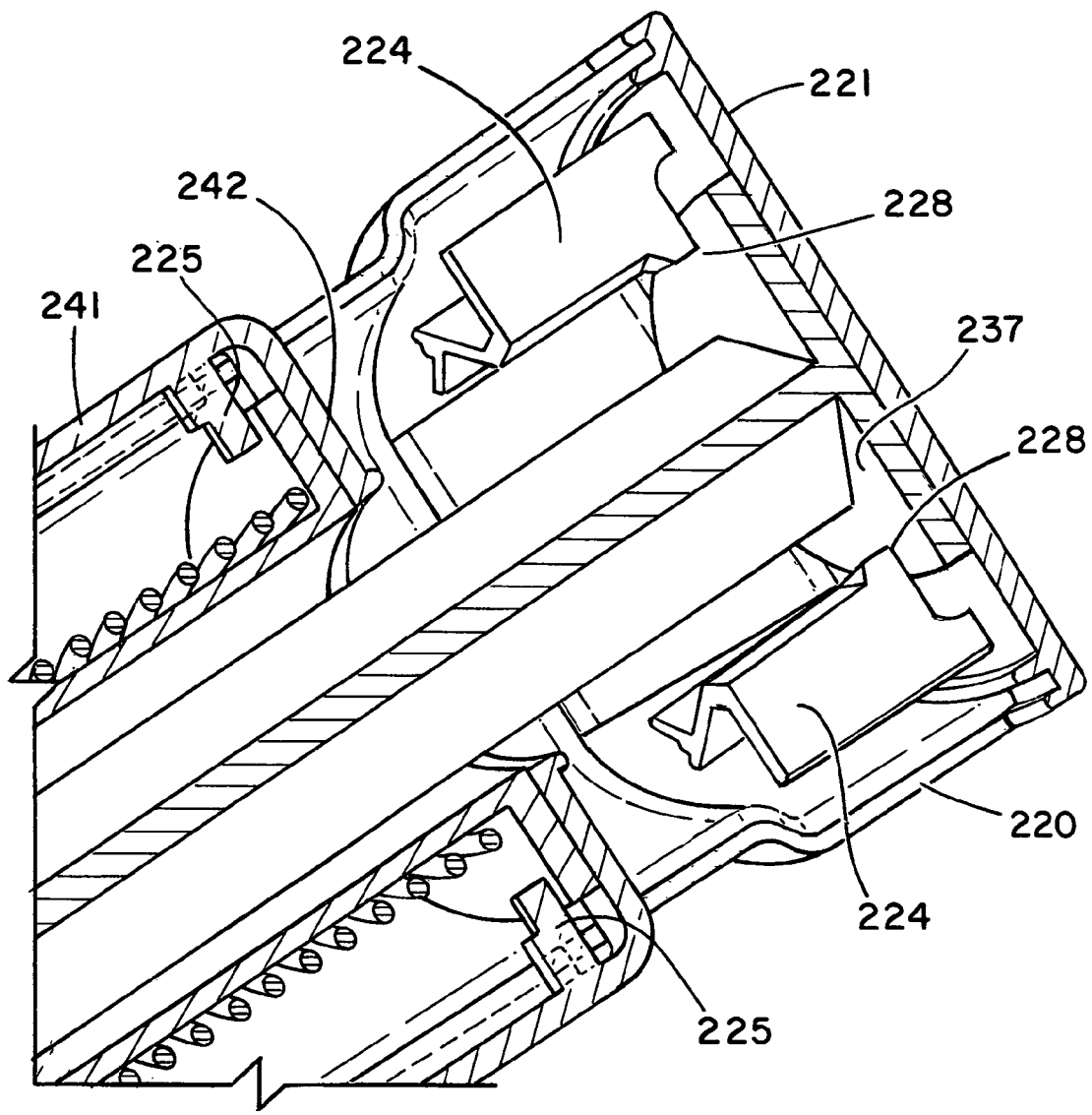
FIG. 4d is a detail cross-sectional view of the end of the syringe housing 220 and cap 221, showing the capture features 228 that mate with the thumb depressor surfaces 237 on the syringe plunger 214 to hold the syringe plunger 214 in place and prevent axial movement of the syringe plunger 214 with respect to the housing 220.

As depicted in FIGS. 4a and 4b, the housing 220 encloses the syringe 209 and has on its open end a cap 221 that fully encloses the housing 220. As shown in FIG. 4c, the cap 221 is snapped and held in place to the end of the housing 220 with snap engagement feature 227. As shown in FIG. 4d, integrated into the cap 221 are capture features 228 that mate with the thumb depressor surfaces 237 on the syringe plunger 214, acting to hold the syringe plunger 214 in place, substantially preventing axial movement of the syringe plunger 214 with respect to the housing 220. Also integrated into the cap 221 are standoffs 224 that limit the travel of the syringe barrel 211 and slider 240. Although the plunger seal 212 could stop against the end of the syringe barrel 211, this is not preferred, as a sustained compressive force of the plunger seal 212 on the syringe barrel 211, as provided by the spring 230 in its passive state, would encourage the syringe 211 material to deform over time. Hence another travel stop, such as the standoffs 224 is preferred.

The housing 220 is preferably formed of injection-molded plastic. The housing 220 must have sufficient strength to support the force applied by the user to compress the spring, plus a safety factor to ensure that the user does not inadvertently break the device by applying too much force to the slider 240. The typical strength required for the housing 220 is in the 10-25 pound range.

The housing 220 may be opaque so as to hide the syringe 209 from view or transparent or translucent so as to allow the syringe to be seen. If the housing 220 hides the syringe 209 from view, an opening or window may be provided in the wall of the housing in the area near the syringe barrel 211, so as to allow the user to see the fluid-holding chamber 215 or the graduation marks on the syringe barrel 211 for the purposes of visually determining the amount of fluid inside the dosage reservoir 200; alternately, the exterior surface of the housing 220 may incorporate graduation marks that can be read against the position of the slider 240 to indicate the amount of fluid inside the dosage reservoir 200. The housing 220 has one end 222 arranged for pushing on a surface when the user is sliding the slider 240. The housing 220 provides an opening 223 through which the dosage conduit 210 passes, providing a fluid connection between the syringe 209 inside the housing and the portions of the first and second fluid flow paths that are arranged outside the housing. The housing 220 also includes a travel stop ledge 229 that limits the travel of the syringe barrel 211. As the user pulls the slider 240, the syringe barrel slides until the thumb depressor feature 237 contacts the travel stop ledge 229. The two travel stops 229 and standoffs 224 limit the travel of the syringe barrel in both directions such that the volume of the fluid holding chamber 215 is accurately controlled.

Figure 4E:
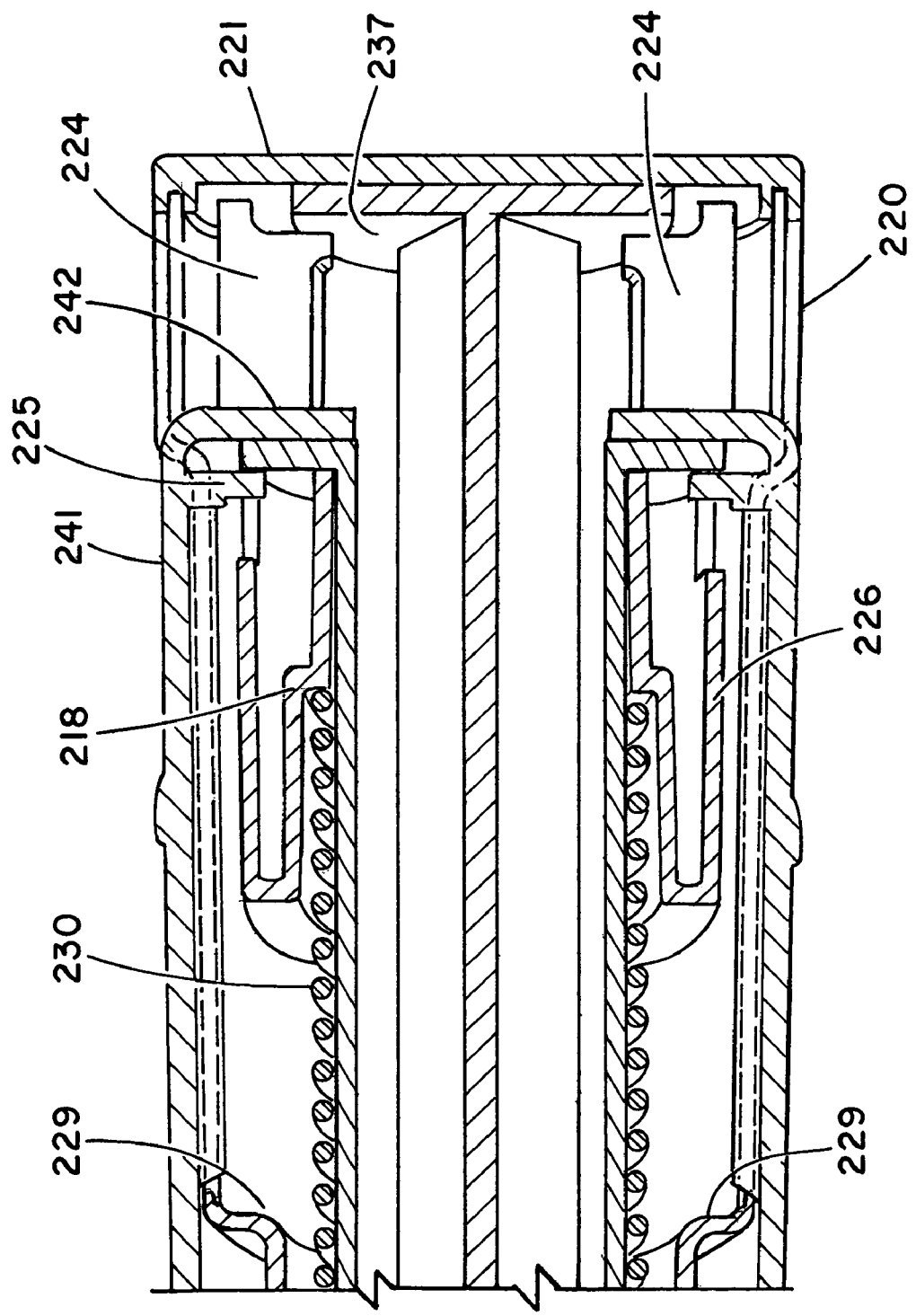
FIG. 4e is a detail cross-sectional view of the end of the syringe housing 220 and cap 221, showing a spacer component 226 that can be used to limit the travel of the syringe barrel 211 over the syringe plunger 214.

As shown in FIG. 4e, a spacer component 226 may be used to limit the travel of the syringe barrel 211 over the syringe plunger 214. The length of this spacer component 226 consumes room required for moving parts, and by limiting the distance sliding parts may move, it also limits the maximum volume of the fluid holding chamber 215. For example, suppose the syringe 211 were of a commercially available variety and could hold a maximum of 6 ml, and this volume was achieved by retracting the plunger 214 from the syringe barrel 211 by 6 cm. If it were desired to design a device with a maximum dosage volume of 5 ml, one could use this 6 ml syringe while controlling the distance between features 229 and 224 such that travel was limited to 5 cm. If a 3 cm long spacer component 226 were added to the assembly, then there would be only 2 cm of travel remaining, and thus the device could fill to a maximum of 2 ml. Therefore, adding such a spacer component 226 during assembly is a simple and cost effective method to produce a device with a smaller dosage volume. The spacer component 226 or similar feature may be produced from any solid material, and may designed and built in any variety of configurations. For example, it could be molded into the housing or one of the other components such that it limits travel to only the slightest movement. Break-away notches could be provided in this spacer such that during manufacture, the length of this spacer feature is cut to a predetermined length, thereby limiting the fluid holding chamber 215 to a maximum volume.

A spring purchase 218 is preferably integrated into this spacer component 226. This height of this purchase is preferably about half the height of the spring purchase itself. The purpose of this is to control the average spring force applied during the duration of the dosage fluid delivery. For example, suppose that without any spacer component 226, the fluid holding chamber 215 is constrained to a maximum volume of 5 ml. At the start of fluid delivery from the dosage reservoir 200, the spring is highly compressed and might produce a fluid pressure of 14 psi. Just before the fluid runs out, the spring is less compressed, and might produce a fluid pressure of 10 psi. Thus the average fluid pressure over the course of delivery is 12 psi. By design, this dosage/bolus fluid pressure should produce the desired average dosage/bolus flow rate, perhaps 10 ml/hr. If another configuration of the device is desired to be constructed with a maximum 2.5 ml dosage volume and an average fluid pressure of 12 psi, one can achieve this average pressure by designing the height of the spring purchase at half the spacer component 226 height. In this example, at the start of fluid delivery, the fluid pressure would be 13 psi, and just before fluid runs out, the fluid pressure would be 11 psi, thus producing an average pressure of 12 psi.

Figure 4F:
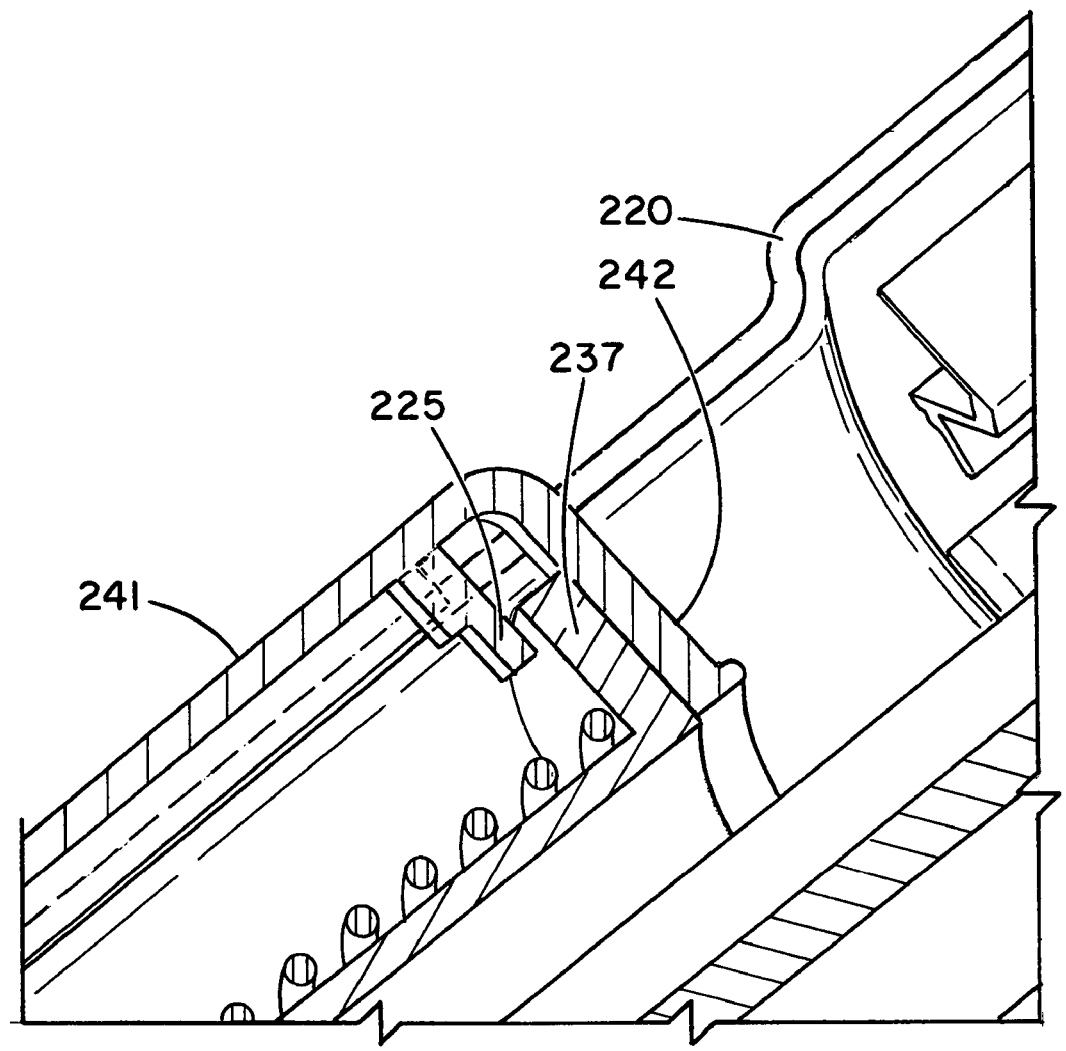
FIG. 4f is a detail cross-sectional view of a portion of the end of the syringe housing 220 showing capture tabs 225 and built into the slider 241.

As shown in FIG. 4f, another useful optional feature built into slider 241 are capture tabs 225. Sandwiched between these capture tabs 225 and the internal portion of the slider 241 is the thumb depressor feature 242 of the syringe barrel 211. The purpose of this feature is to hold the slider 241 and the syringe barrel 211 together. Without the capture tabs 225, and particularly after the dosage reservoir has been actuated, as illustrated in FIG. 5b, there would be freedom for the slider 241 to slide or rattle back and forth. As this is not desirable, capture tabs 225 are included in the design. For safety, the capture tabs 225 are designed to bend or break away at low forces. This is to prevent a user from pushing the slider 241 towards cap 221, thereby possibly raising the fluid pressure higher than intended.

A spring 230 is also held inside the housing 220, such that one end of the spring is held in a fixed position with respect to the housing 220, while the other end can move axially with respect to the housing as the spring expands and contracts. The other end of the spring engages the syringe barrel 211 and thereby creates the dosage reservoir pressure within the fluid-holding chamber 215 of the syringe 209. The spring is depicted in FIGS. 4a and 4b as a coiled compression spring. However, a reader skilled in the art will recognize that, with minimal re-arranging of the major components of the dosage reservoir 200, other spring styles may be effectively used. Examples of alternate springs include but are not limited to: a coiled extension spring, an extensible elastomeric band, a compressible elastomeric column, a compressed-air or compressed-gas spring, a stacked-washer spring (e.g., wave spring or belleville spring), a coiled flat spring (i.e., "Negator" or constant-force spring). The spring force and spring rate (i.e., how the spring force changes as the spring is extended or compressed) are selected and controlled during manufacturing to provide the desired dosage reservoir pressure. A slider 240 is provided, with an external portion 241 positioned about the periphery of the housing 220 such that the user can freely grasp or otherwise engage the slider 240, and an internal portion 242 positioned inside the housing 220 such that it engages the syringe barrel 211. The user selectively and temporarily removes the spring force from the syringe barrel 211 by sliding the slider 240 with respect to the housing 220, thereby compressing the spring 230. The slider 240 is preferably formed of injection-molded plastic, and must have sufficient strength to support the force applied by the user to compress the spring, plus a safety factor to ensure that the user does not inadvertently break the device by applying too much force to the slider 240. The typical strength required for the slider 240 is in the 10-25 pound range.

Figure 7A:
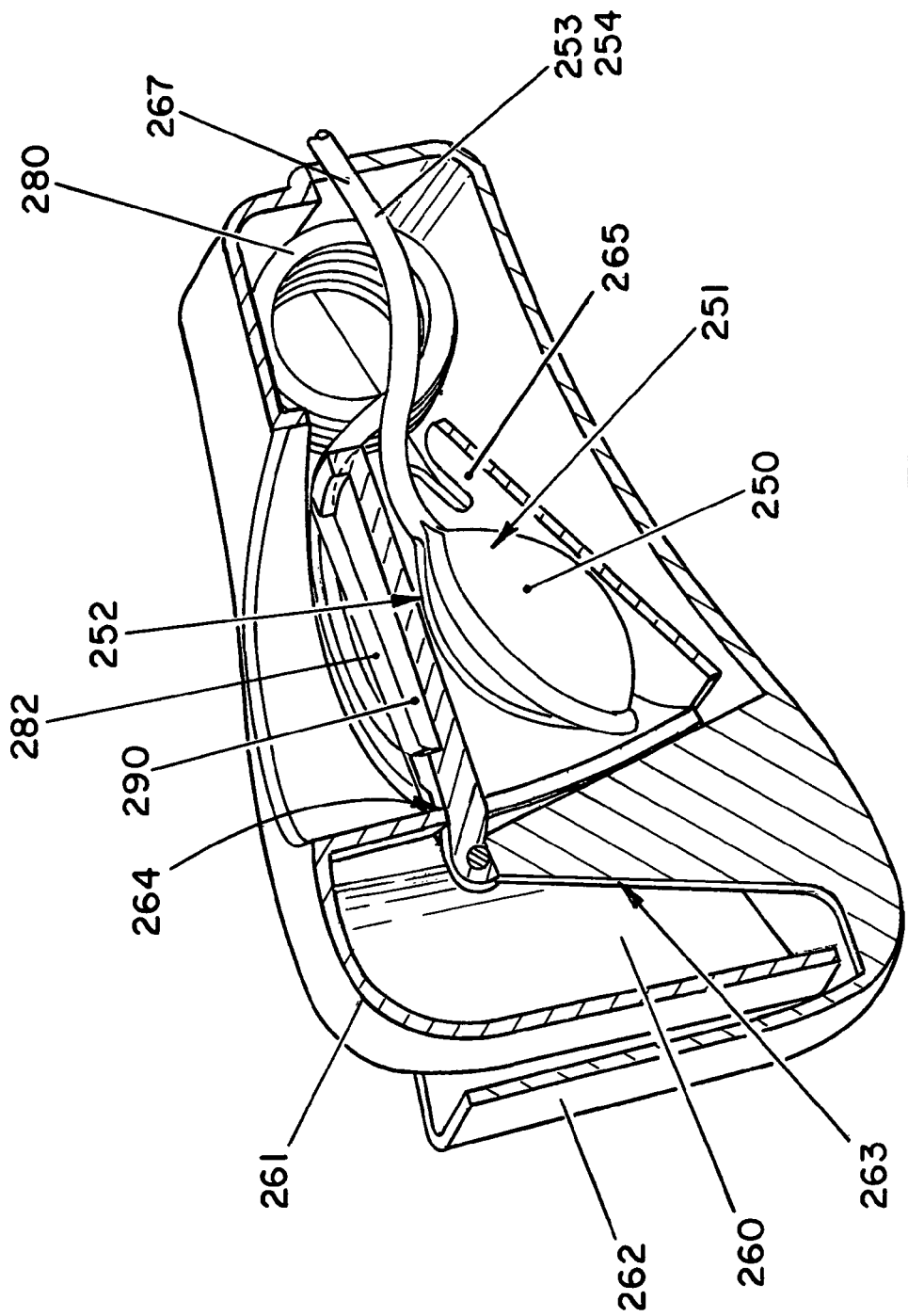
FIG. 7a is a cross-sectional view of a bag-style dosage reservoir filled with fluid.
Figure 7B:
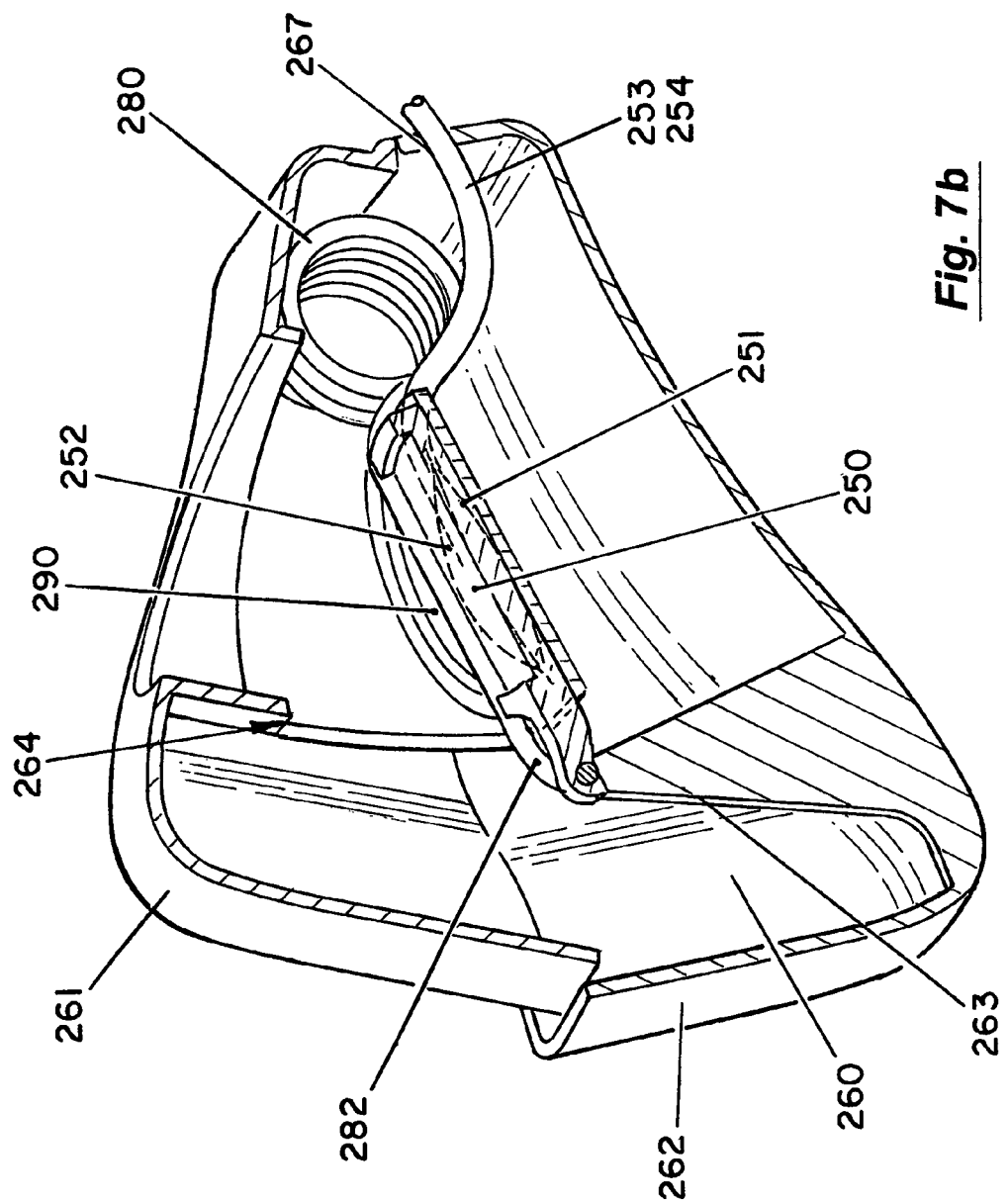
FIG. 7b is a cross-sectional view of the bag-style dosage reservoir in its empty state.

FIGS. 7a and 7b show cross-sectional views of another of the many potential physical embodiments of the dosage reservoir 200 that would fall under the scope of the invention as depicted schematically in FIGS. 1 and 3. This particular embodiment of the dosage reservoir 200 incorporates a flexible bag pressurized with a spring and held inside a housing that comprises a squeeze mechanism for selectively removing the spring force from the bag. The dosage reservoir 200 depicted in FIGS. 7a and 7b is comprised of a flexible bag 250 held inside a hinged housing 260 arranged such that the flexible bag 250 sits inside a fixed recess 265 formed within the first side 261 of the hinged housing 260. A spring 280 is arranged within the hinged housing 260 such that the upper spring arm(s) 281 bear against the inner surface of the housing and the lower spring arm(s) 282 bear against a movable plate 290. The movable plate 290 bears on one side of the flexible bag 250, such that the flexible bag is compressed between the movable plate 290 and the fixed recess 265 and effectively pressurized by the force of the spring 280. The hinged housing 260 allows the user to selectively and temporarily remove the spring force to de-pressurize the flexible bag 250. This de-pressurization of the flexible bag 250 allows the dosage reservoir 200 to fill. The user depressurizes the flexible bag 250 by squeezing the two sides 261 and 262 of the hinged housing 260 together; as the two sides 261 and 262 come together, a raised tab 263 on the second side 262 engages the second spring arm 282 and lifts it toward the inner surface of the first side 261, thereby compressing the spring and lifting the movable plate 290 away from the flexible bag 250.

The hinged housing 260 is preferably formed of injection-molded plastic, and is shown in FIGS. 7a and 7b as a one-piece design with a hinge 266 molded into the plastic between the molded regions forming the two sides 261 and 262. A multiple-piece design wherein the two sides 261 and 262 are molded as separate pieces and connected together at the hinge 266 during manufacturing is also acceptable. The hinged housing 260 must have sufficient strength to support the force applied by the user to compress the spring, plus a safety factor to ensure that the user does not inadvertently break the device by applying too much force. The typical strength required for the hinged housing 260 is in the 10-25 pound range. The hinged housing 260 may be opaque so as to hide the flexible bag 250 from view or transparent or translucent so as to allow the bag to be seen. If the hinged housing 260 hides the flexible bag 250 from view, an opening or window may be provided in the wall of the housing in the area near the fixed recess 265, so as to allow the user to see the flexible bag 250 for the purposes of visually determining the amount of fluid inside the dosage reservoir 200. Alternately, the exterior surface of the hinged housing 260 may incorporate graduation marks that can be read against the relative position of the two sides 261 and 262 with respect to each other, to indicate the amount of fluid inside the dosage reservoir 200. The hinged housing 260 is sized and shaped to fit in the user's hand, and arranged such that a squeezing motion of the user's hand accomplishes the squeezing together of the two sides 261 and 262. The hinged housing 260 incorporates a stop 264. When the user depressurizes the flexible bag 250 by squeezing the two sides 261 and 262 of the hinged housing 260 together, and thereby lifting the movable plate 290 away from the flexible bag 250, the travel of the movable plate 290 is limited by the stop 264. The position of the stop 264 controls how far the movable plate 290 can be lifted (with respect to the fixed recess 265 and the position of the flexible bag 250), and therefore controls how far the flexible bag 250 can expand as it fills with fluid. The combination of this control on the movement of the movable plate 290, the dimensions of the fixed recess 265, and the dimensions of the flexible bag 250 serve to establish the maximum volume of fluid that can be held inside the flexible bag 250, and thereby control the volume of the controlled-volume dosage reservoir 200. The hinged housing 260 provides an opening 267 through which the first and second flexible tubes 253 and 254 pass, providing a fluid connection between the flexible bag 250 inside the housing and the portions of the first and second fluid flow paths that are arranged outside the housing.

Preferably, the flexible bag 250 is an assembly formed of a first flexible web 251 and a second flexible web 252 sealed together about the periphery to form the flexible bag 250, with a first flexible tube 253 and a second flexible tube 254 sealed between the two flexible webs and providing a fluid inlet and fluid outlet, respectively, to the flexible bag 250. The flexible bag 250 is substantially flat when empty, with the flexible webs parallel and in close planar proximity to each other; as the flexible bag 250 fills, the flexible webs move apart to accommodate the fluid between them, and the bag becomes substantially 3-dimensional. The flexible webs are preferably sealed in a substantially round shape, but other shapes such as rectangular, oval, or others are acceptable. The flexible webs are preferably formed of a common, medical grade plastic such as PVC, EVA, polyethylene, or polyurethane; alternate materials are acceptable provided that they meet the biocompatibility and drug compatibility requirements of the therapeutic application in which the finished device is used. While the flexible bag 250 is depicted as described above in FIGS. 6a and 6b, it should be recognized that, with minimal re-arranging of the major components of the dosage reservoir 200, other flexible container styles may be effectively used. Examples of alternative flexible bags include but are not limited to: a substantially flat or substantially 3-dimensional pouch formed of a flexible material (such as a dip-molded or blow-molded component), a bellows, a length of flexible-walled tubing. The first and second flexible tubes 253 and 254, providing the fluid inlet and outlet to the flexible bag 250, provide a connection between the dosage reservoir 200 and the rest of the device, and are part of the first and second fluid paths discussed and illustrated in FIGS. 1-4. A single flexible tube may be used instead of the first and second flexible tubes 253 and 254. This third tube preferably connects to the first and second flow paths (connecting the dosage reservoir to the medication reservoir and distal outlet respectively) by use of a 3-way adapter 350. The spring 230 is depicted in FIGS. 7a and 7b as a coiled torsion spring. However, a reader skilled in the art will recognize that, with minimal re-arranging of the major components of the dosage reservoir 200, other spring styles may be effectively used. Examples of alternate springs include but are not limited to: a coiled compression spring, a coiled extension spring, an extensible elastomeric band, a compressible elastomeric column, a compressed-air or compressed-gas spring, a stacked-washer spring (e.g., wave spring or belleville spring). The spring force and spring rate (i.e., how the spring force changes as the spring is extended or compressed) are selected and controlled during manufacturing to provide the desired dosage reservoir pressure.

Figure 8A:
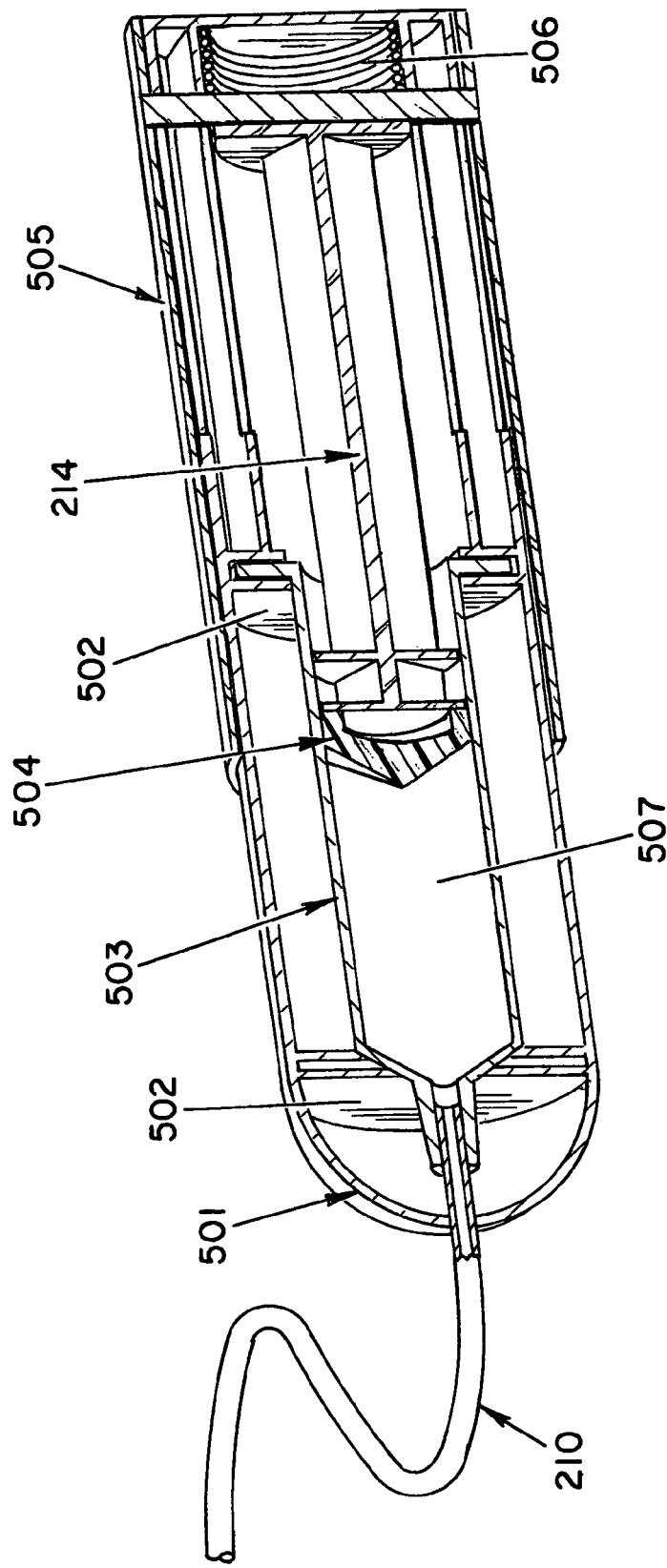
FIG. 8a is a cross-sectional view of another embodiment of a syringe-style dosage reservoir filled with fluid.
Figure 8B:
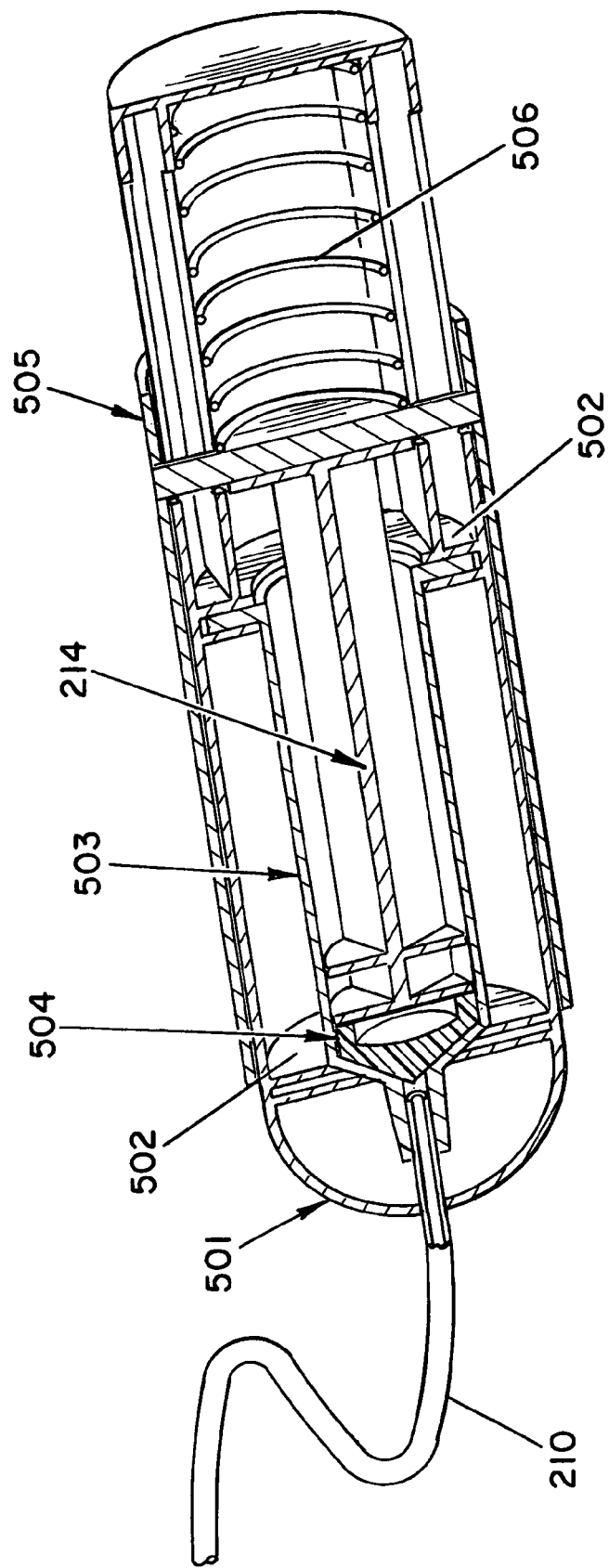
FIG. 8b is a cross-sectional view of the syringe-style dosage reservoir in FIG. 8a in its empty state.

Illustrated in FIG. 8 is an embodiment of dosage reservoir 200 similar to that shown in FIGS. 4 and 5. FIG. 8a shows the fluid holding chamber 507 full with the spring 506 applying pressure to the plunger 214. FIG. 8b shows the fluid holding chamber 507 empty, with the spring 506 partially open. The following items are notable in this embodiment, and differ from the embodiment in FIGS. 4 and 5 in several ways. The syringe barrel 503 remains stationary with respect to the housing 501. Engagement features 502 which are part of the housing 501 mate with the syringe barrel 503 to substantially prevent axial movement of the syringe barrel (instead allowing the syringe plunger 214 to move). To pressurize the dosage reservoir, the spring 506 bears against the syringe plunger 214, rather than against the syringe barrel 503. The slider 505 engages the syringe plunger 214 or the spring 506, rather than engaging the syringe barrel 503. The slider 505 may be arranged to engage the syringe plunger 214, such that the user actively draws the syringe plunger 214 back when sliding the slider 505. This configuration has the effect of increasing the speed with which the fluid-holding chamber 507 fills with fluid, as the force applied by the user to the slider acts to overcome the sliding friction between the syringe plunger seal 504 and syringe barrel 503, and also acts to create negative pressure within the fluid-holding chamber 507, thereby increasing the pressure drop from the medication reservoir 100 and increasing the fluid flow rate between the medication reservoir 100 and the dosage reservoir 200. Alternately, the slider 505 may be arranged to engage spring 506 only, such that when the user slides the slider 505 the user is only compressing the spring and the syringe plunger 214 is left in its original position. This configuration has the effect of decreasing the speed with which the fluid-holding chamber 507 fills with fluid, as the medication reservoir pressure must overcome the frictional force of the sliding friction between the syringe plunger seal 504 and syringe barrel 503. However, this configuration also has the effect of decreasing the amount of force that the user must apply to slide the slider 505, because the user is not required to overcome the syringe friction or to apply the force required to draw a negative pressure within the fluid-holding chamber 507.

Figure 9A:
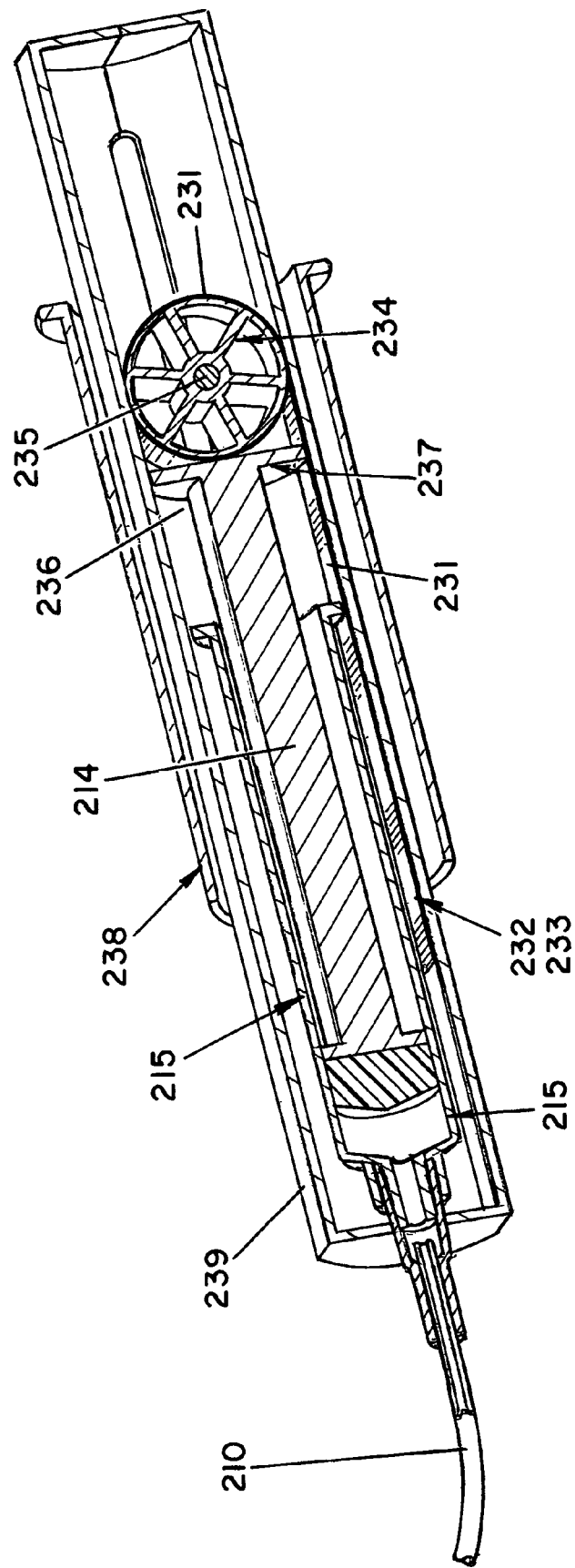
FIGS. 9a and 9b are cross-sectional views of yet another embodiment of a syringe-style dosage reservoir in perpendicular planes.
Figure 9B:
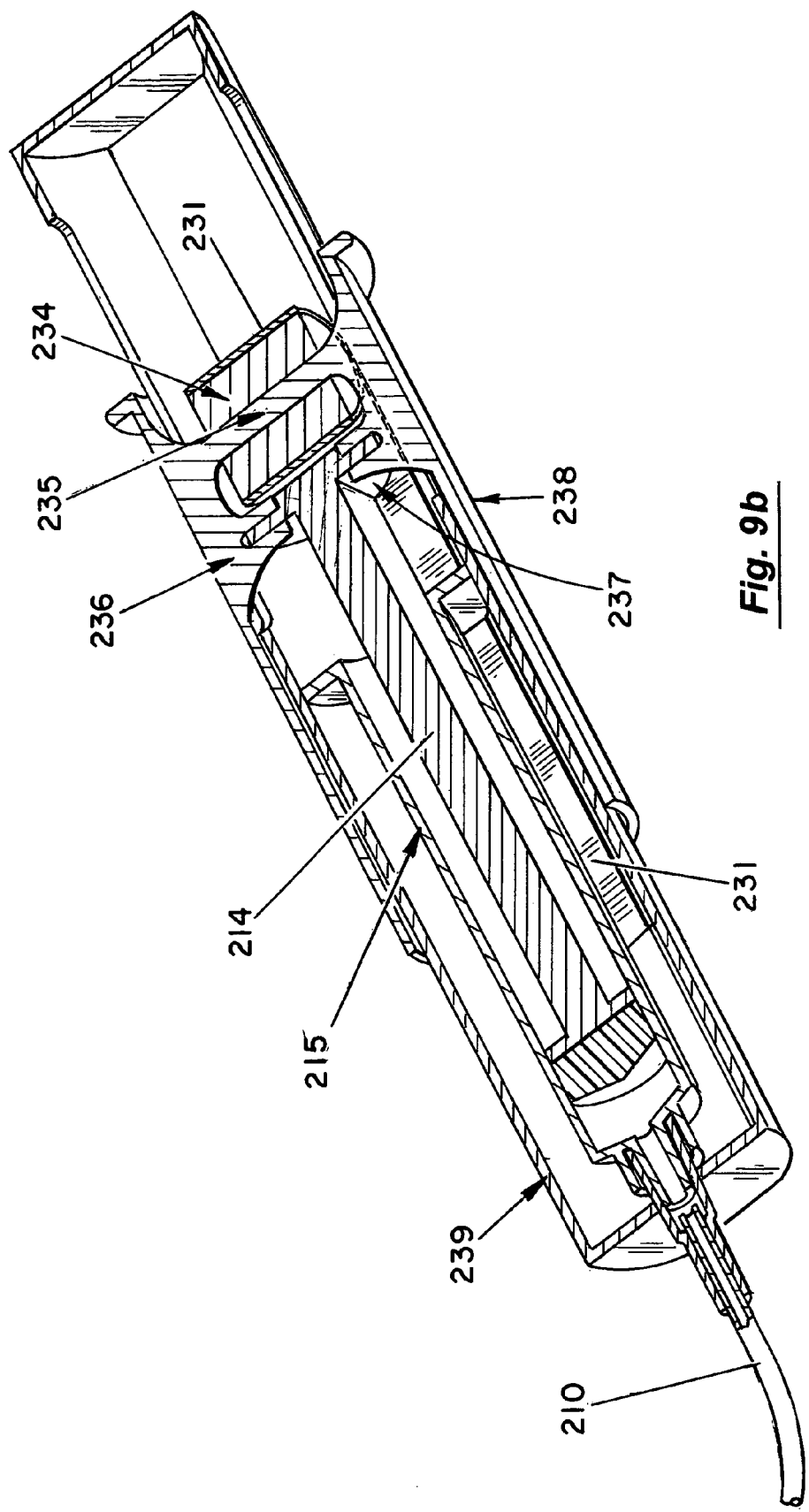
Figure 9C:
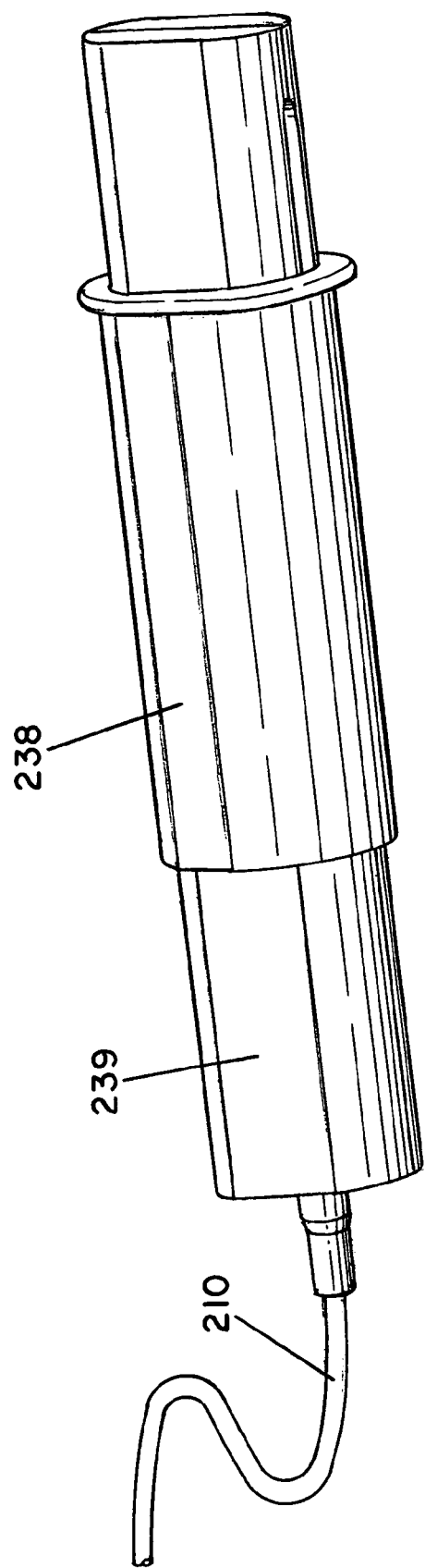
FIG. 9c is a perspective view of the embodiment of the syringe-style dosage reservoir shown in FIGS. 9a and 9b.

FIGS. 9a, 9b and 9c illustrate another embodiment of the dosage reservoir 200. FIGS. 9a and 9b are cross sectional views of FIG. 9c in perpendicular planes, and in these figures the fluid holding chamber 215 is approximately 20% full. This embodiment is similar to the one in FIG. 8 in that they both utilize a syringe barrel 211 that is fixed with respect to the housing 239. The key difference is that in the FIG. 8 embodiment, a coil spring 230 pushes the syringe plunger 214, and in the FIG. 9 embodiment, a constant force spring 231 pushes on the syringe plunger 214. At one end of the constant force spring 231 is an engagement feature 232 that is fixed to a matching engagement feature 233 on the housing 239. The other end of the constant force spring 231 is wrapped over rotating hub 234, which is centered over shaft 235, and shaft 235 is a molded feature of slider 238. The spring 231 is biased to being in the wrapped state; hence, it pulls the hub 234, shaft 235, and slider 238 toward housing engagement feature 233 with a controlled force. As motion begins toward the engagement feature 233, the spring 231 wraps over hub 234, which rotates over shaft 235. Integrated into the slider 238 are additional engagement features 236 that mate with the plunger thumb depressor 237. Thus, as slider 238 is pulled back away from the dosage conduit 210, the shaft 235 pulls the hub 235 and spring 231 open. As the slider 238 is released, the spring 231 pulls the hub 235, slider 238, and plunger 214 along with it. This compresses the fluid holding chamber 215 and creates the dosage reservoir pressure. This pressure is substantially maintained until the fluid holding chamber 215 is empty.

Figure 10A:
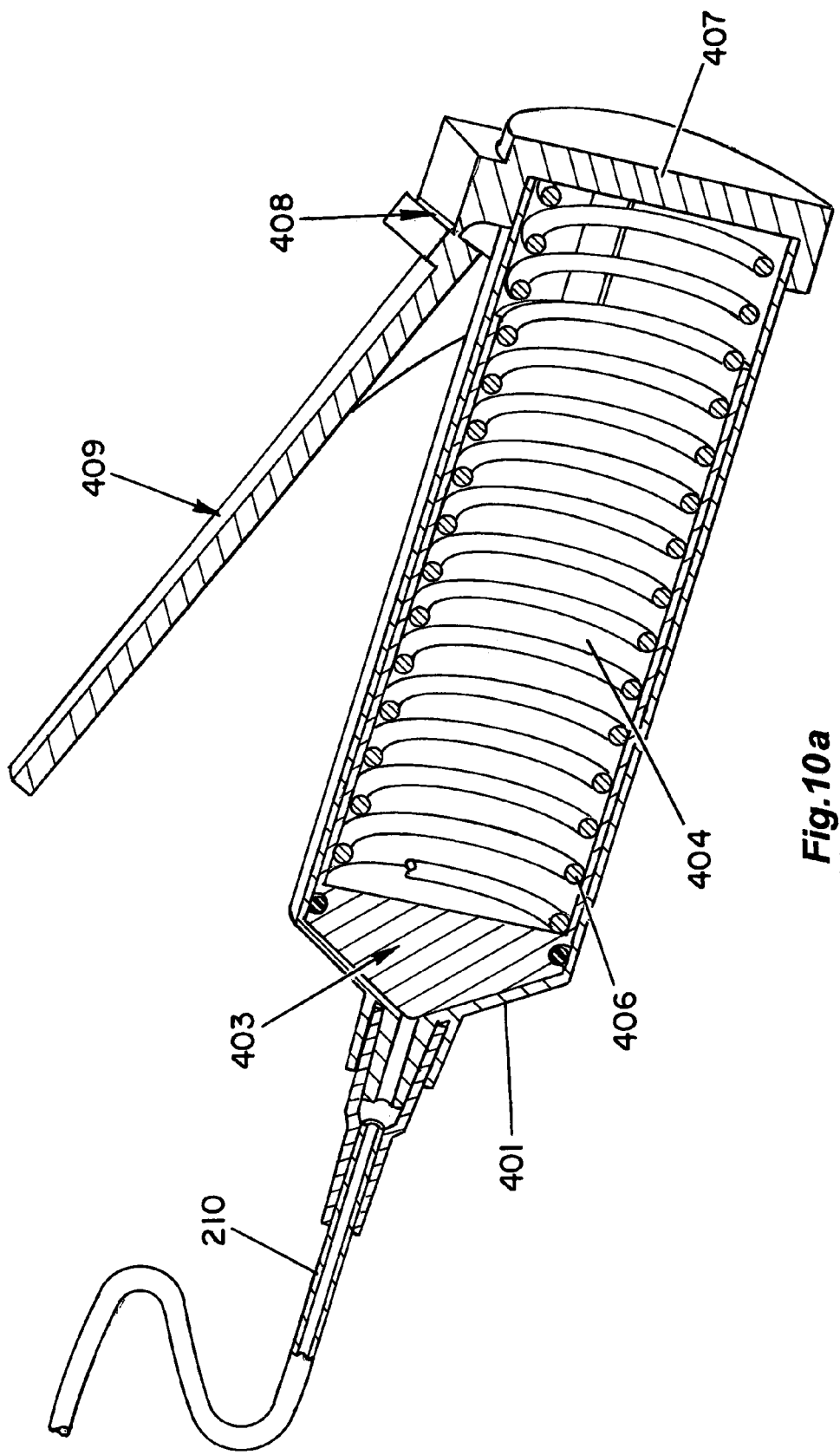
FIG. 10a is a cross-sectional view of yet another embodiment of a syringe-style dosage reservoir.
Figure 10B:
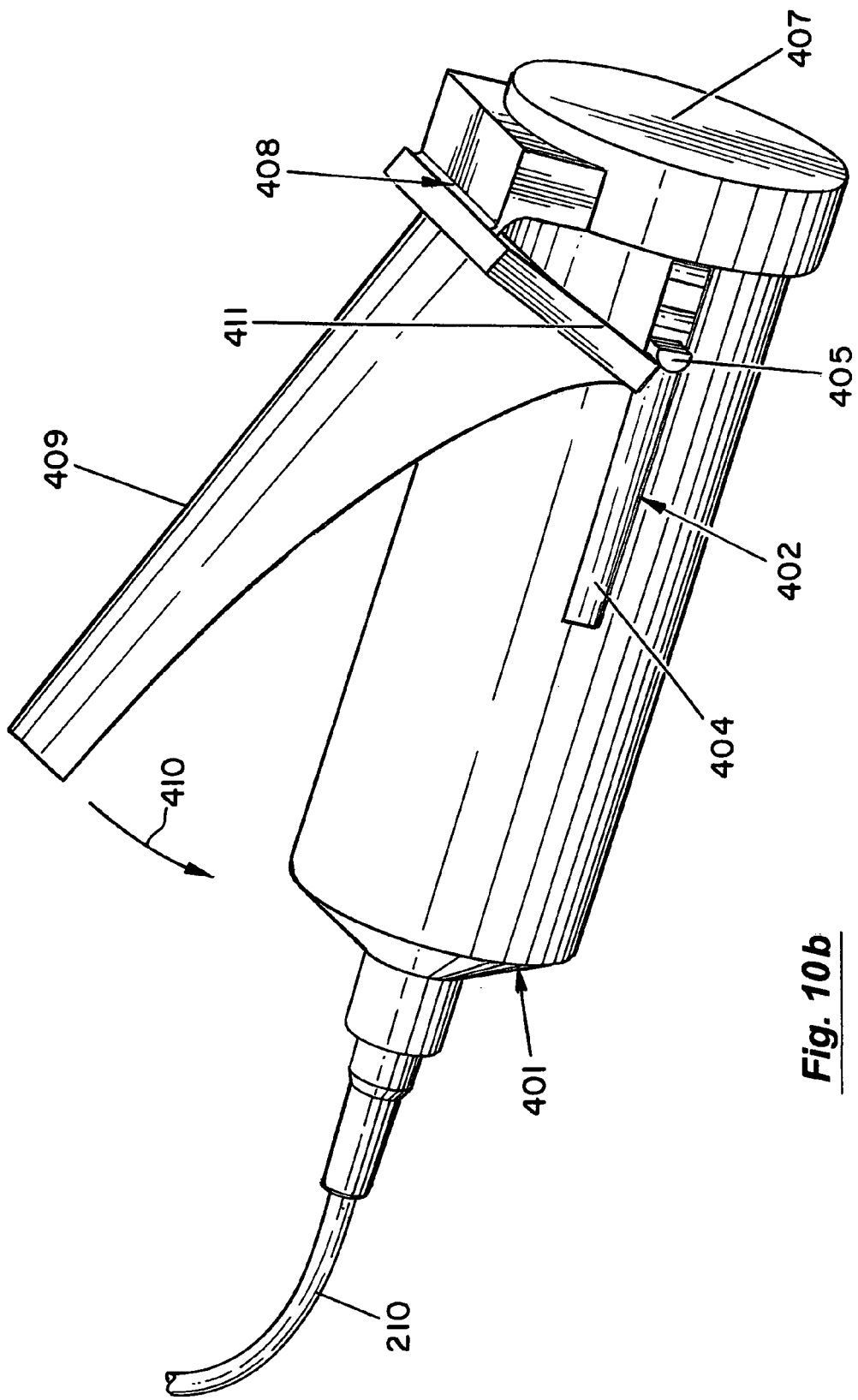

FIGS. 10a and 10b illustrate another one of many possible embodiments that fall under the scope of this invention. FIG. 10a is a cross sectional view of FIG. 10b. In this embodiment, the syringe barrel 401 acts as a housing, containing the fluid, the plunger 403, and spring 406. The syringe barrel 401 is configured with slots 402 at the open end, which properly orient plunger tabs 405. The plunger 403 is configured with long cup 404, which contains the spring 406. At the open end of the plunger cup 404, are two tabs 405 that fit into the slots 402. The spring 406 and plunger 403 are constrained in the syringe barrel 401 by means of a cap 407 which may be fastened to the barrel 401 in a variety of methods. A squeeze lever 409 is rotatably fastened to the cap 407 via a hinge mechanism 408. As the squeeze lever 409 is squeezed in direction 410, slide features 411 push on tabs 405. This compresses the spring 406, thus drawing fluid into the syringe barrel 401 from dosage conduit 210. As the lever 409 is released, the spring 406 exerts a force on the fluid to create the dosage pressure. This pressure, which is higher than the medication reservoir pressure, causes the flow rate through the flow restrictor 700 to increase to a bolus flow rate, until the syringe barrel 401 is empty.

Figure 11A:
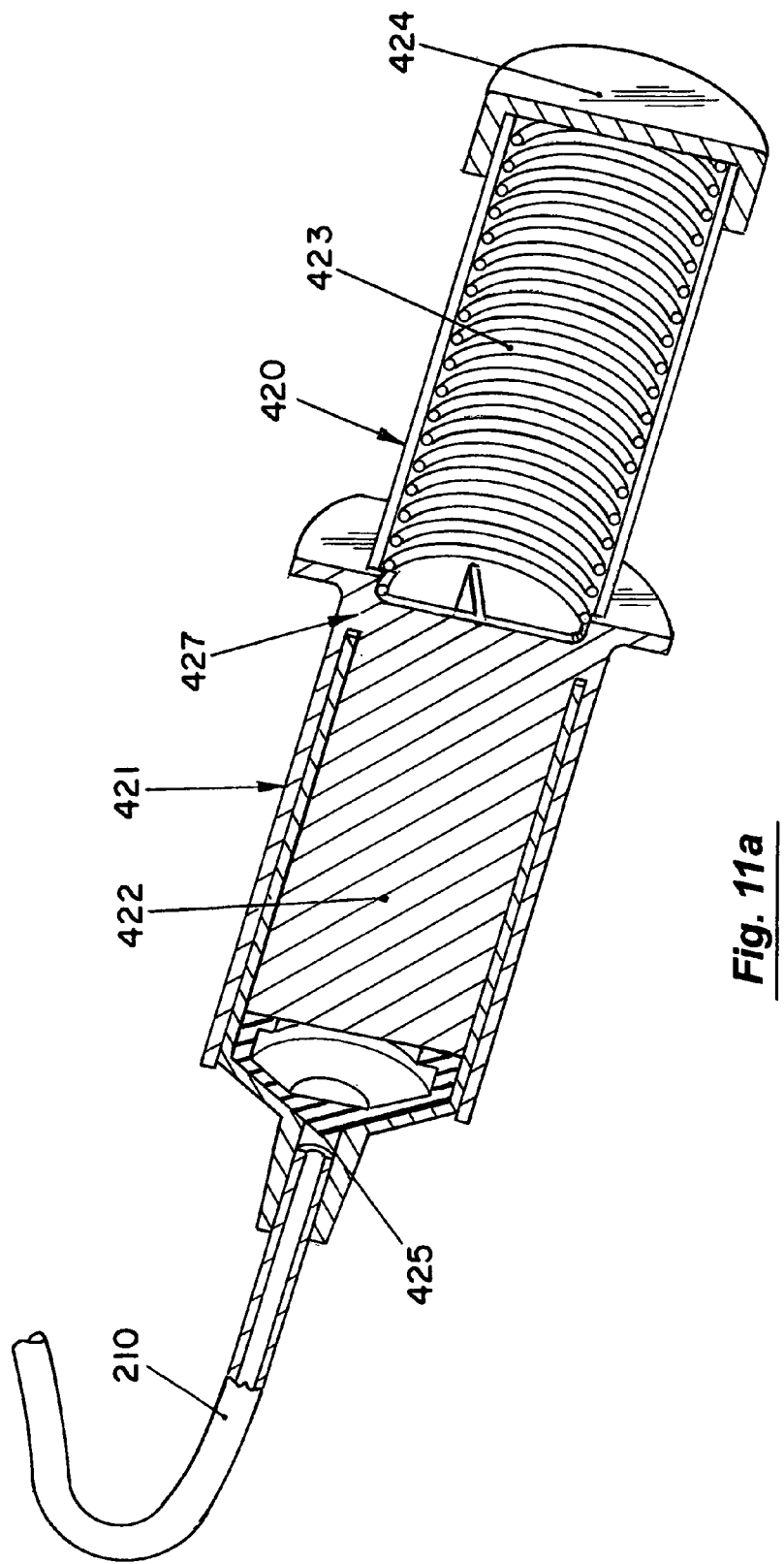
FIG. 11a is a cross-sectional view of yet another embodiment of a syringe-style dosage reservoir in which the spring is directly compressed by the slider 421.
Figure 11B:
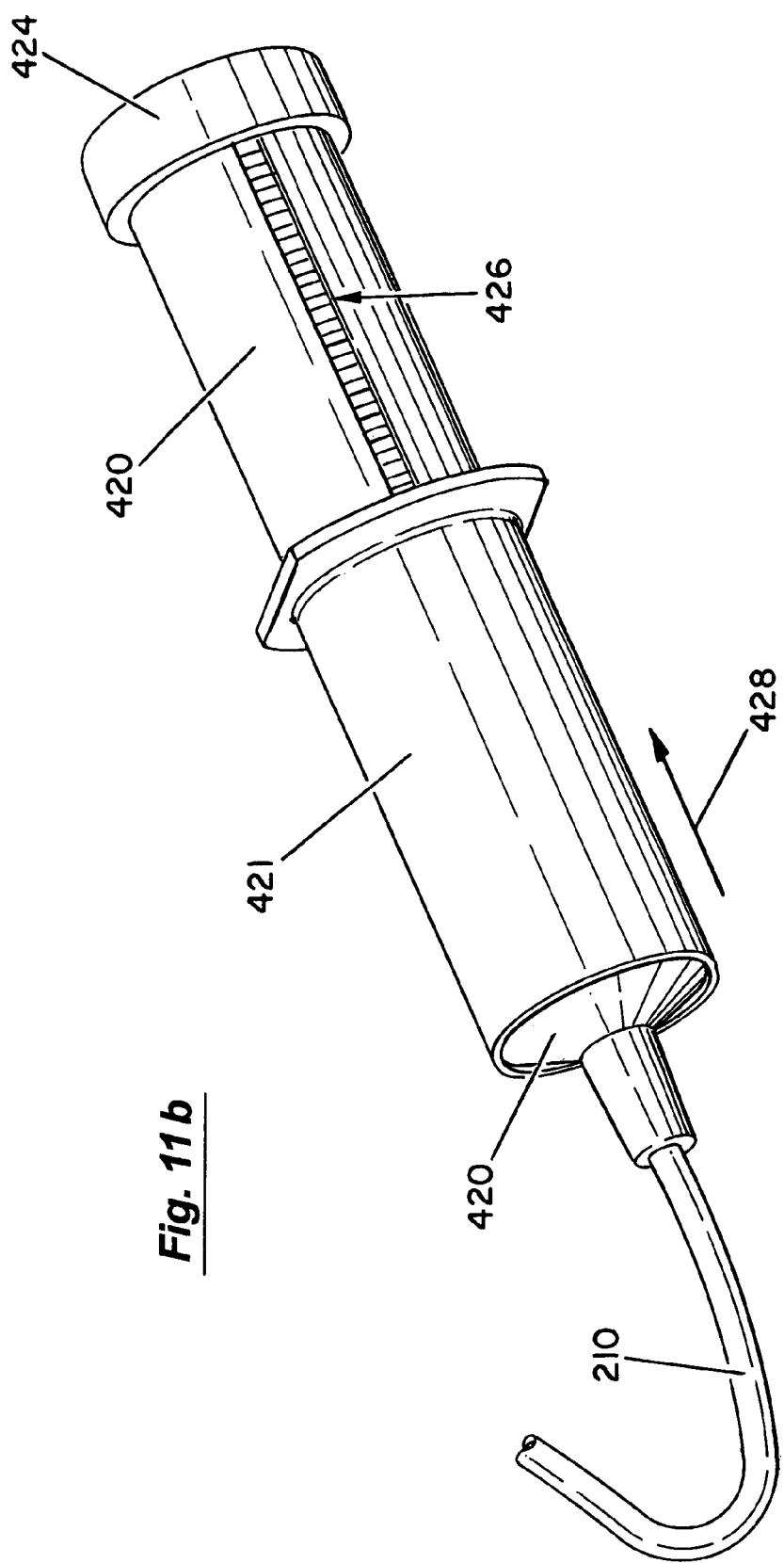

FIGS. 11a and 11b illustrate another one of many possible embodiments that fall under the scope of this invention. FIG. 11a is a cross sectional view of FIG. 11b. This embodiment is similar to the one in FIG. 10 in that they both utilize a spring that directly acts upon the plunger. The key difference is that in the FIG. 10 embodiment, the mechanical advantage of a hinged lever 409 is utilized to compress a spring; and in the embodiment in FIG. 11, the spring is directly compressed by the slider without any mechanical advantage. The embodiment in FIG. 10 would be more appropriate for a large-diameter syringe barrel, and the embodiment in FIG. 11 is more appropriate for a smaller-diameter syringe barrel. The operation of this embodiment is also similar to that described in FIG. 8. The slider 421 is pulled in the direction of actuation 428, and the internal members of the slider 422 push upon spring 423. There is a bridging member 427 of the slider 421 that runs through the slots 426 and connects the outer "grip" portion with the internal members 422. If the internal members 422 are fastened to the plunger tip 425, pulling the slider acts to also pull the plunger tip 425 along with the slider. If the internal members 422 are not fastened to the plunger tip 425, the pressure differential between the medication reservoir 100 and the dosage reservoir 200 is adequate to push the plunger in the same direction as the slider. As the plunger moves away from the distal end of the syringe barrel 420, it rapidly fills with medication from the medication reservoir 100 via the dosage conduit 210. As the slider 421 is released by the user, the spring 423 exerts a controlled force on the internal members 422 and the plunger tip 425, which creates a controlled degree of fluid pressure in the syringe. Since this controlled pressure is higher than the medication reservoir pressure, the flow rate through the flow restrictor 700 is also higher. When the fluid has emptied the syringe, the fluid pressure returns to that of the medication reservoir, and the flow rate returns to its continuous state.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

We claim:

1. An infusion device for delivery of a controlled-volume dosage of a fluid to a patient, said infusion device comprising:
    a medication reservoir delivering fluid at a pressure;
    a dosage reservoir having an initial, substantially empty state;
    a first fluid conduit between the medication reservoir and dosage reservoir;
    a one-way valve allowing fluid flow through the first fluid conduit only away from the medication reservoir;
    a pressure source applying pressure higher than the medication reservoir pressure to gradually dispense fluid from the dosage reservoir;
    an actuator manually movable against pressure applied by the pressure source to temporarily reduce the pressure applied by the pressure source and enable the dosage reservoir to rapidly fill with a controlled volume of fluid from the medication reservoir through the first fluid conduit;
    a patient connection;
    a second fluid conduit between the dosage reservoir and the patient connection; and
    a flow restrictor restricting the fluid flow rate from the dosage reservoir through the second fluid conduit to the patient connection, whereby the fluid flow rate is determined by the fluid pressure provided by the medication reservoir and the dosage reservoir.

2. The infusion device of claim 1 wherein a basal flow rate is delivered to the patient connection resulting from the medication reservoir pressure while the dosage reservoir is empty and a greater bolus flow rate is temporarily delivered to the patient connection resulting from the dosage reservoir pressure after actuation, and wherein the ratio of the basal flow rate to the bolus flow rate is determined by the ratio of the medication reservoir pressure to the dosage reservoir pressure.

3. The infusion device of claim 1 wherein the dosage reservoir comprises a syringe.

4. The infusion device of claim 3 wherein the pressure source comprises a spring biasing the syringe toward an empty state.

5. The infusion device of claim 1 wherein the actuator comprises a slider to temporarily reduce the pressure applied by the pressure source.

6. The infusion device of claim 1 wherein the actuator comprises a squeeze lever to temporarily check the pressure source.

7. The infusion device of claim 1 wherein the dosage reservoir comprises a flexible bag.

8. The infusion device of claim 1 wherein the dosage reservoir comprises a bellows.

9. The infusion device of claim 1 wherein the actuator comprises a push button to temporarily check the pressure source.

10. The infusion device of claim 1 wherein the dosage reservoir comprises a rolling diaphragm.

11. The infusion device of claim 1 wherein the dosage reservoir further comprises indicia showing the amount of fluid in the dosage reservoir.

12. The infusion device of claim 1 wherein the dosage reservoir further comprises an adjustment mechanism for adjusting the volume of the dosage reservoir.

13. An infusion device for delivery of a controlled-volume dosage of a fluid to a patient, said infusion device comprising:
    a medication reservoir delivering fluid at a pressure;
    a dosage reservoir having an initial, substantially empty state;
    a patient connection;
    a 3-leg adapter providing a three-way fluid connection;
    a first fluid conduit between the medication reservoir and the 3-leg adapter;
    a second fluid conduit between the 3-leg adapter and the patient connection;
    a third fluid conduit between the 3-leg adapter and the dosage reservoir;
    a one-way valve allowing fluid flow through the first fluid conduit only from the medication reservoir to the 3-leg adapter;
    a pressure source applying pressure, higher that the medication reservoir pressure, to gradually dispense the fluid from the dosage reservoir;
    an actuator manually movable against pressure applied by the pressure source to temporarily reduce the pressure applied by the pressure source and thereby enable the dosage reservoir to rapidly fill with a controlled volume of fluid from the medication reservoir through the first fluid conduit and third fluid conduit; and
    a flow restrictor restricting the flow rate from the dosage reservoir through the second fluid conduit, whereby the flow rate delivered to the patient is determined by the fluid pressure provided by the medication reservoir and the dosage reservoir.

14. The infusion device of claim 13 wherein the flow restrictor is selected to deliver a basal flow rate determined by the medication reservoir pressure with the dosage reservoir in an empty state.

15. The infusion device of claim 14 wherein the flow restrictor is selected to deliver a bolus flow rate from the fluid pressure provided by the pressurized dosage reservoir after actuation, and wherein the bolus flow rate is greater than the basal flow rate.

16. The infusion device of claim 15 wherein the ratio of the basal flow rate to the bolus flow rate is determined by the ratio of the medication reservoir pressure to the dosage reservoir pressure.

17. The infusion device of claim 13 wherein the dosage reservoir comprises a syringe.

18. The infusion device of claim 17 wherein the pressure source comprises a spring biasing the syringe toward the empty state.

19. The infusion device of claim 13 wherein the actuator comprises a slider to temporarily reduce the pressure applied by the pressure source.

20. The infusion device of claim 13 wherein the dosage reservoir comprises a flexible bag.

21. The infusion device of claim 13 wherein the dosage reservoir comprises a bellows.

22. The infusion device of claim 13 wherein the dosage reservoir comprises a rolling diaphragm.

23. The infusion device of claim 13 wherein the actuator comprises a push button to temporarily check the pressure source.

24. The infusion device of claim 13 wherein the actuator comprises a squeeze lever to temporarily check the pressure source.

25. The infusion device of claim 13 wherein the dosage reservoir further comprises indicia showing the amount of fluid in the dosage reservoir.

26. The infusion device of claim 13 wherein the dosage reservoir comprises an adjustment mechanism for adjusting the volume of the dosage reservoir.

* * * * *